(12) United States Patent
Walker et al.

(10) Patent No.: US 9,745,566 B2
(45) Date of Patent: Aug. 29, 2017

(54) RECOMBINANT MICROORGANISMS AND METHODS OF USE THEREOF

(71) Applicant: LanzaTech New Zealand Limited, Skokie, IL (US)

(72) Inventors: David Jeffrey Fraser Walker, Boston, MA (US); Shilpa Nagaraju, Lincolnwood, IL (US); Michael Koepke, Chicago, IL (US); Alexander Paul Mueller, Chicago, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 291 days.

(21) Appl. No.: 14/484,402

(22) Filed: Sep. 12, 2014

(65) Prior Publication Data
US 2015/0072395 A1   Mar. 12, 2015

Related U.S. Application Data

(60) Provisional application No. 61/877,272, filed on Sep. 12, 2013.

(51) Int. Cl.
| | | |
|---|---|---|
| C12N 15/70 | (2006.01) | |
| A61K 38/00 | (2006.01) | |
| C12N 9/00 | (2006.01) | |
| C12N 15/74 | (2006.01) | |

(52) U.S. Cl.
CPC ............... *C12N 9/93* (2013.01); *C12N 15/74* (2013.01); *C12Y 601/0102* (2013.01)

(58) Field of Classification Search
CPC .......... C12N 9/93; C12N 15/70; A61K 38/00; C09K 2019/3425
See application file for complete search history.

(56) References Cited

U.S. PATENT DOCUMENTS

| | | |
|---|---|---|
| 5,593,886 A | 1/1997 | Gaddy |
| 6,368,819 B1 | 4/2002 | Gaddy et al. |
| 8,143,037 B2 | 3/2012 | Zahn et al. |
| 2013/0045539 A1 | 2/2013 | Delenda et al. |

FOREIGN PATENT DOCUMENTS

| | | |
|---|---|---|
| WO | 2008028055 | 3/2008 |
| WO | 2012053905 | 4/2012 |

OTHER PUBLICATIONS

International Search Report, PCT/US2014/055318, Dec. 17, 2015.
Abrini, Arch Microbiol, 161: 345-351, 1994.
Kopke, Appl Environ Microbiol, 77: 5567-5475, 2011.
Tanner, Int J System Bacteriol, 43: 232-236, 1993.
Tirado-Acevedo, Production of bioethanol from synthesis gas using *Clostridium Ijungdahlii*, PhD thesis, North State University, 2010. Carolina.

*Primary Examiner* — Kagnew H Gebreyesus
(74) *Attorney, Agent, or Firm* — Andrea Schoen

(57) ABSTRACT

The present provides selection markers, methods, nucleic acids, and vectors of use in the preparation of recombinant *Clostridium* spp.

3 Claims, 6 Drawing Sheets

FIG. 3

*E. coli* MG1655 (SEQ ID 20):
MSHLAELVASAKAAISQASDVAALDNVRVEYLGKKGHLTLQMTTLRELPPEERPAAGAVIN
EAKEQVQQALNARKAELESAALNARLAAETIDVSLPGRRIENGGLHPVTRTIDRIESFFGELGF
TVATGPEIEDDYHNFDALNIPGHHPARADHDTFWFDTTRLLRTQTSGVQIRTMKAQQPPIRII
APGRVYRNDYDQTHTPMFHQMEGLIVDTNISFTNLKGTLHDFLRNFFEEDLQIRFRPSYFPFT
EPSAEVDVMGKNGKWLEVLGCGMVHPNVLRNVGIDPEVYS GFAFG
MGMERLTMLRYGVTDLRSFFENDLRFLKQFK

*C. autoethanogenum* (SEQ ID 21):
VKGEFKMKEELKQIKENAFNELKNKKLDIEDIRVKYLGKKGELTKILRGMKDLSKEERPAIG
KLANEVRSTLENAIEEASKKIKSSAIQAKLQNETIDITMPGIKQTVGKRHPLEQTLEEMKQIFIS
MGFTIEEGPEVEKDYYNFEALNIPKNHPARGEQDTFYINDNVVLRTQTSPIQVRTMEKQKPPI
KMISPGKVYRSDSVDATHSPIFYQMEGLVVDKGITFANLKGTLELFAKKLFGNDIRTKFRPHH
FPFTEPSAEMDASCFVCHGKGCRVCKGEGWIELLGCGMVHPQVLRNCGIDPEVYSGFAFGM
GVDRMVMLKYGIDDIRNMYESDMRFLNQF- MG1655_ ----MSHLAELVASAKAAISQASD-
VAALDNVRVEYLGKKGHLTLQMTTLRELPPEERPA 55
LZ1561_
VKGEFKMKEELKQIKENAFNELKNKKLDIEDIRVKYLGKKGELTKILRGMKDLSKEERPA 60
    :  **  . * .:  . :: ********  . :* .*****

MG1655_
AGAVINEAKEQVQQALNARKAELESAALNARLAAETIDVSLPGRRIENGGLHPVTRTIDR 115
LZ1561_
IGKLANEVRSTLENAIEEASKKIKSSAIQAKLQNETIDITMPGIKQTVGKRHPLEQTLEE 120
   * .**:  ..:.*.  . :*.****.:.*  .* . **: .*: .

MG1655_
IESFFGELGFTVATGPEIEDDYHNFDALNIPGHHPARADHDTFWFDTTRLLRTQTSGVQI 175
LZ1561_
MKQIFISMGFTIEEGPEVEKDYYNFEALNIPKNHPARGEQDTFYINDNVVLRTQTSPIQV 180
 :.*   :* . :*:::***...::*: .:.:*******.:*:

MG1655_ RTMKAQQPPIRIIAPGRVYRND-
YDQTHTPMFHQMEGLIVDTNISFTNLKGTLHDFLRNF 234
LZ1561_
RTMEKQKPPIKMISPGKVYRSDSVDATHSPIFYQMEGLVVDKGITFANLKGTLELFAKKL 240
***:.*:***::*.:**.*  * *  :**:..* **:*:.  :

MG1655_ FEEDLQIRFRPSYFPFTEPSAEVDV------MGK------NGK-
WLEVLGCGMVHPNVLRNV 283
LZ1561_
FGNDIRTKFRPHHFPFTEPSAEMDASCFVCHGKGCRVCKGEGWIELLGCGMVHPQVLRNC
300
  *..:  .*..***: .             . :*******:.*

MG1655_ GIDPEVYSGFAFGMGMERLTMLRYGVTDLRSFFENDLRFLKQFK 327
LZ1561_ GIDPEVYSGFAFGMGVDRMVMLKYGIDDIRNMYESDMRFLNQF- 343

SEQUENCE LISTING

```
<160> NUMBER OF SEQ ID NOS: 58

<210> SEQ ID NO 1
<211> LENGTH: 3418
<212> TYPE: DNA
<213> ORGANISM: Artificial sequence
<220> FEATURE:
<223> OTHER INFORMATION: Nucleic acid sequence of plasmid pMK-RQ-Hs-tk

<400> SEQUENCE: 1
ctaaattgta agcgttaata ttttgttaaa attcgcgtta aatttttgtt aaatcagctc        60
attttttaac caataggccg aaatcggcaa atcccttat aaatcaaaag aatagaccga       120
gatagggttg agtggccgct acagggcgct cccattcgcc attcaggctg cgcaactgtt       180
gggaagggcg tttcggtgcg ggcctcttcg ctattacgcc agctggcgaa aggggggatgt       240 gctgcaaggc gattaagttg ggtaacgcca gggttttccc agtcacgacg ttgtaaaacg       300
acggccagtg agcgcgacgt aatacgactc actatagggc gaattgaagg aaggccgtca       360
aggccgcatc atatggcttc gtaccctgc catcaacacg cgtctgcgtt cgaccaggct       420
gcgcgttctc gcggccatag caaccgacgt acggcgttgc gccctcgccg gcagcaagaa       480
gccacggaag tccgcccgga gcagaaaatg cccacgctac tgcgggttta tatagacggt       540
ccccacggga tggggaaaac caccaccacg caactgctgt ggcccctggg ttcgcgcgac       600
gatatcgtct acgtacccga gccgatgact tactggcggg tgctgggggc ttccgagaca       660
atcgcgaaca tctacaccac acaacaccgc ctcgaccagg tgagatatc ggccggggac       720 gcggcggtgg taatgacaag cgcccagata acaatgggca tgccttatgc cgtgaccgac       780
gccgttctgg ctcctcatat cgggggggag gctgggagct cacatgcccc gccccggcc       840 ctcaccctca tcttcgaccg ccatcccatc gccgccctcc tgtgctaccc ggccgcgcgg       900
taccttatgg gcagcatgac cccccaggcc gtgctggcgt tcgtggccct catcccgccg       960
accttgcccg gcacaaacat cgtgttgggg gcccttccgg aggacagaca catcgaccgc      1020
ctggccaaac gccagcgccc cggtgagcgg cttgacctgg ctatgctggc cgcgattcgc      1080
cgcgtttacg ggctacttgc caatacggtg cggtatctgc agtgcggcgg gtcgtggcgg      1140
gaggattggg gacagctttc gggagcggcc ttgacgcccc agggtgccga gccccagagc      1200
aacgcgggcc cacgacccca tatcggggaa acgttattta ccctgtttcg ggcccccgag      1260
ttgctggccc ccaacggcga cctgtacaac gtgtttgcct gggccttgga cgtcttggcc      1320
aaacgcctcc gtcccatgca cgtctttatc ctggattacg accaatcgcc cgccggctgc      1380
cgggacgccc tgctgcaact tacctccggg atggtccaga cccatgtcac caccccaggc      1440
tccataccga cgatctgcga cctggcgcgc acgtttgccc gggagatggg ggaggctcac      1500
tgagctagcc tgggcctcat gggccttcct ttcactgccc gctttccagt cgggaaacct      1560
gtcgtgccag ctgcattaac atggtcatag ctgtttcctt gcgtattggg cgctctccgc      1620
ttcctcgctc actgactcgc tgcgctcggt cgttcgggta aagcctgggg tgcctaatga     1680
```

```
gcaaaaggcc agcaaaaggc caggaaccgt aaaaaggccg cgttgctggc gttttttccat   1740 aggctccgcc cccctgacga gcatcacaaa atcgacgct caagtcagag gtggcgaaac    1800
ccgacaggac tataaagata ccaggcgttt ccccctggaa gctcccctcgt gcgctctcct   1860 gttccgaccc tgccgcttac cggatacctg tccgcctttc tcccttcggg aagcgtggcg   1920
ctttctcata gctcacgctg taggtatctc agttcggtgt aggtcgttcg ctccaagctg   1980
ggctgtgtgc acgaaccccc cgttcagccc gaccgctgcg ccttatccgg taactatcgt   2040
cttgagtcca acccggtaag acacgactta tcgccactgg cagcagccac tggtaacagg   2100
attagcagag cgaggtatgt aggcggtgct acagagttct tgaagtggtg cctaactac    2160 ggctacacta gaagaacagt atttggtatc tgcgctctgc tgaagccagt taccttcgga   2220
aaaagagttg gtagctcttg atccggcaaa caaaccaccg ctggtagcgg tggtttttt    2280 gtttgcaagc agcagattac gcgcagaaaa aaggatctc aagaagatcc tttgatcttt    2340
tctacggggt ctgacgctca gtggaacgaa aactcacgtt aagggatttt ggtcatgaga   2400
ttatcaaaaa ggatcttcac ctagatcctt ttaaattaaa aatgaagttt taaatcaatc   2460
taaagtatat atgagtaaac ttggtctgac agttattaga aaaattcatc cagcagacga   2520
taaaacgcaa tacgctggct atccggtgcc gcaatgccat acagcaccag aaaacgatcc   2580
gcccattcgc cgcccagttc ttccgcaata tcacgggtgg ccagcgcaat atcctgataa   2640
cgatccgcca cgcccagacg gccgcaatca ataaagccgc taaaacggcc attttccacc   2700
ataatgttcg gcaggcacgc atcaccatgg gtcaccacca gatcttcgcc atccggcatg   2760
ctcgctttca gacgcgcaaa cagctctgcc ggtgccaggc cctgatgttc ttcatccaga   2820
tcatcctgat ccaccaggcc cgcttccata cgggtacgcg cacgttcaat cgatgtttc    2880 gcctgatgat caaacggaca ggtcgccggg tccagggtat gcagacgacg catggcatcc   2940
gccataatgc tcacttttc tgccggcgca agatggctag acagcagatc ctgacccggc   3000
acttcgccca gcagcagcca atcacggccc gcttcggtca ccacatccag caccgccgca   3060
cacggaacac cggtggtggc cagccagctc agacgcgccg cttcatcctg cagctcgttc   3120
agcgcaccgc tcagatcggt tttcacaaac agcaccggac gaccctgcgc gctcagacga   3180
aacaccgccg catcagagca gccaatggtc tgctgcgccc aatcatagcc aaacagacgt   3240
tccacccacg ctgccgggct acccgcatgc aggccatcct gttcaatcat actcttcctt   3300
tttcaatatt attgaagcat ttatcagggt tattgtctca tgagcggata catatttgaa   3360
tgtatttaga aaaataaaca aatagggggtt ccgcgcacat ttccccgaaa agtgccac    3418
```

<210> SEQ ID NO 2
<211> LENGTH: 5821
<212> TYPE: DNA
<213> ORGANISM: Artificial sequence
<220> FEATURE:
<223> OTHER INFORMATION: Nucleic acid sequence of plasmid pMTL83155-Hs-tk

<400> SEQUENCE: 2

```
cctgcaggat aaaaaaattg tagataaatt ttataaaata gttttatcta caatttttt     60 atcaggaaac agctatgacc gcggccgcaa tatgatattt atgtccattg tgaaagggat   120
tatattcaac tattattcca gttacgttca tagaaatttt cctttctaaa atattttatt   180
ccatgtcaag aactctgttt atttcattaa agaactataa gtacaaagta taaggcattt   240
gaaaaaatag gctagtatat tgattgatta tttattttaa aatgcctaag tgaaatatat   300
```

```
acatattata acaataaaat aagtattagt gtaggatttt taaatagagt atctattttc    360
agattaaatt tttgattatt tgatttacat tatataaat tgagtaaagt attgactagc    420 aaaattttt gatactttaa tttgtgaaat ttcttatcaa agttatatt tttgaataat    480 ttttattgaa aaatacaact aaaaaggatt atagtataag tgtgtgtaat tttgtgttaa    540
atttaaaggg aggaaatgaa catgaaacat atggcttcgt accctgcca tcaacacgcg    600 tctgcgttcg accaggctgc gcgttctcgc ggccatagca accgacgtac ggcgttgcgc    660
cctcgccggc agcaagaagc cacggaagtc cgcccggagc agaaaatgcc cacgctactg    720
cgggtttata tagacggtcc ccacgggatg gggaaaacca ccaccacgca actgctggtg    780
gccctgggtt cgcgcgacga tatcgtctac gtacccgagc cgatgactta ctggcgggtg    840 ctggggctt ccgagacaat cgcgaacatc tacaccacac aacaccgcct cgaccagggt    900
gagatatcgg ccggggacgc ggcggtggta atgacaagcg cccagataac aatgggcatg    960
ccttatgccg tgaccgacgc cgttctggct cctcatatcg gggggaggc tgggagctca    1020 catgccccgc cccggccct caccctcatc ttcgaccgcc atcccatcgc cgccctcctg    1080
tgctacccgg ccgcgcggta ccttatgggc agcatgaccc ccaggccgt gctggcgttc    1140 gtggccctca tcccgccgac cttgcccggc acaaacatcg tgttggggc cttccggag    1200 gacagacaca tcgaccgcct ggccaaacgc cagcgcccg tgagcggct tgacctggct    1260 atgctggccg cgattcgccg cgtttacggg ctacttgcca atacggtgcg gtatctgcag    1320
tgcggcgggt cgtggcggga ggattgggga cagctttcgg gagcggcctt gacgccccag    1380
ggtgccgagc cccagagcaa cgcgggccca cgaccccata tcggggaaac gttatttacc    1440
ctgtttcggg ccccgagtt gctggccccc aacggcgacc tgtacaacgt gtttgcctgg    1500
gccttggacg tcttggccaa acgcctccgt cccatgcacg tctttatcct ggattacgac    1560
caatcgcccg ccggctgccg ggacgccctg ctgcaactta cctccgggat ggtccagacc    1620
catgtcacca ccccaggctc cataccgacg atctgcgacc tggcgcgcac gtttgcccgg    1680
gagatggggg aggctcactg agctagcata aaaataagaa gcctgcattt gcaggcttct    1740 tattttatg gcgcgccgcc attattttt tgaacaattg acaattcatt tcttattttt    1800
tattaagtga tagtcaaaag gcataacagt gctgaataga agaaattta cagaaaagaa    1860 aattatagaa tttagtatga ttaattatac tcatttatga atgtttaatt gaatacaaaa    1920
aaaaatactt gttatgtatt caattacggg ttaaaatata gacaagttga aaaatttaat    1980
aaaaaaataa gtcctcagct cttatatatt aagctaccaa cttagtatat aagccaaaac    2040
ttaaatgtgc taccaacaca tcaagccgtt agagaactct atctatagca atatttcaaa    2100
tgtaccgaca tacaagagaa acattaacta tatatattca atttatgaga ttatcttaac    2160
agatataaat gtaaattgca ataagtaaga tttagaagtt tatagccttt gtgtattgga    2220
agcagtacgc aaaggctttt ttatttgata aaaattagaa gtatatttat tttttcataa    2280
ttaatttatg aaaatgaaag ggggtgagca aagtgacaga ggaaagcagt atcttatcaa    2340
ataacaaggt attagcaata tcattattga ctttagcagt aaacattatg actttatag    2400 tgcttgtagc taagtagtac gaaaggggga gcttaaaaa gctccttgga atacatagaa    2460
ttcataaatt aatttatgaa agaagggcg tatatgaaaa cttgtaaaaa ttgcaaagag    2520
tttattaaag atactgaaat atgcaaaata cattcgttga tgattcatga taaacagta    2580 gcaacctatt gcagtaaata caatgagtca agatgtttac ataaagggaa agtccaatgt    2640
```

```
attaattgtt caaagatgaa ccgatatgga tggtgtgcca taaaaatgag atgttttaca    2700
gaggaagaac agaaaaaaga acgtacatgc attaaatatt atgcaaggag ctttaaaaaa    2760
gctcatgtaa agaagagtaa aagaaaaaa taatttattt attaatttaa tattgagagt    2820
gccgacacag tatgcactaa aaaatatatc tgtggtgtag tgagccgata caaaaggata    2880
gtcactcgca ttttcataat acatcttatg ttatgattat gtgtcggtgg gacttcacga    2940
cgaaaaccca caataaaaaa agagttcggg gtagggttaa gcatagttga ggcaactaaa    3000
caatcaagct aggatatgca gtagcagacc gtaaggtcgt tgtttaggtg tgttgtaata    3060
catacgctat taagatgtaa aaatacggat accaatgaag ggaaaagtat aattttggga    3120
tgtagtttgt ttgttcatct atgggcaaac tacgtccaaa gccgtttcca aatctgctaa    3180
aaagtatatc ctttctaaaa tcaaagtcaa gtatgaaatc ataaataaag tttaattttg    3240
aagttattat gatattatgt ttttctatta aaataaatta agtatataga atagtttaat    3300
aatagtatat acttaatgtg ataagtgtct gacagtgtca cagaaaggat gattgttatg    3360
gattataagc ggccggccag tgggcaagtt gaaaaattca caaaaatgtg gtataatatc    3420
tttgttcatt agagcgataa acttgaattt gagagggaac ttagatggta tttgaaaaaa    3480
ttgataaaaa tagttggaac agaaaagagt attttgacca ctactttgca agtgtaccct    3540
gtacctacag catgaccgtt aaagtggata tcacacaaat aaaggaaaag ggaatgaaac    3600
tatatcctgc aatgctttat tatattgcaa tgattgtaaa ccgccattca gagtttagga    3660
cggcaatcaa tcaagatggt gaattgggga tatatgatga gatgatacca agctatacaa    3720
tatttcacaa tgatactgaa acattttcca gcctttggac tgagtgtaag tctgacttta    3780
aatcattttt agcagattat gaaagtgata cgcaacggta tggaaacaat catagaatgg    3840
aaggaaagcc aaatgctccg gaaaacattt ttaatgtatc tatgataccg tggtcaacct    3900
tcgatggctt taatctgaat ttgcagaaag gatatgatta tttgattcct atttttacta    3960
tggggaaata ttataaagaa gataacaaaa ttatacttcc tttggcaatt caagttcatc    4020
acgcagtatg tgacggattt cacatttgcc gttttgtaaa cgaattgcag gaattgataa    4080
atagttaact tcaggtttgt ctgtaactaa aaacaagtat ttaagcaaaa acatcgtaga    4140
aatacggtgt tttttgttac cctaagttta aactccttt tgataatctc atgaccaaaa    4200
tcccttaacg tgagttttcg ttccactgag cgtcagaccc cgtagaaaag atcaaaggat    4260
cttcttgaga tcctttttt ctgcgcgtaa tctgctgctt gcaaacaaaa aaaccaccgc    4320
taccagcggt ggtttgtttg ccggatcaag agctaccaac tcttttccg aaggtaactg    4380
gcttcagcag agcgcagata ccaaatactg ttcttctagt gtagccgtag ttaggccacc    4440
acttcaagaa ctctgtagca ccgcctacat acctcgctct gctaatcctg ttaccagtgg    4500
ctgctgccag tggcgataag tcgtgtctta ccgggttgga ctcaagacga tagttaccgg    4560
ataaggcgca gcggtcgggc tgaacggggg gttcgtgcac acagcccagc ttggagcgaa    4620
cgacctacac cgaactgaga tacctacagc gtgagctatg agaaagcgcc acgcttcccg    4680
aagggagaaa ggcggacagg tatccggtaa gcggcagggt cggaacagga gagcgcacga    4740
gggagcttcc agggggaaac gcctggtatc tttatagtcc tgtcgggttt cgccacctct    4800
gacttgagcg tcgatttttg tgatgctcgt caggggggcg gagcctatgg aaaaacgcca    4860
gcaacgcggc ctttttacgg ttcctggcct tttgctggcc ttttgctcac atgttctttc    4920
ctgcgttatc ccctgattct gtggataacc gtattaccgc ctttgagtga gctgataccg    4980
ctcgccgcag ccgaacgacc gagcgcagcg agtcagtgag cgaggaagcg gaagagcgcc    5040
```

```
caatacgcag ggcccectgc ttcggggtca ttatagcgat ttttcgta tatccatcct    5100 ttttcgcacg atatacagga ttttgccaaa gggttcgtgt agactttcct tggtgtatcc    5160
aacggcgtca gccgggcagg ataggtgaag taggcccacc cgcgagcggg tgttccttct    5220
tcactgtccc ttattcgcac ctggcggtgc tcaacgggaa tcctgctctg cgaggctggc    5280
cggctaccgc cggcgtaaca gatgagggca agcggatggc tgatgaaacc aagccaacca    5340
ggaagggcag cccacctatc aaggtgtact gccttccaga cgaacgaaga gcgattgagg    5400
aaaaggcggc ggcggccggc atgagcctgt cggcctacct gctggccgtc ggccagggct    5460
acaaaatcac gggcgtcgtg gactatgagc acgtccgcga gctggcccgc atcaatggcg    5520
acctgggccg cctgggcggc ctgctgaaac tctggctcac cgacgacccg cgcacggcgc    5580
ggttcggtga tgccacgatc ctcgccctgc tggcgaagat cgaagagaag caggacgagc    5640
ttggcaaggt catgatgggc gtggtccgcc cgagggcaga gccatgactt ttttagccgc    5700
taaaacggcc gggggtgcg cgtgattgcc aagcacgtcc ccatgcgctc catcaagaag    5760
agcgacttcg cggagctggt gaagtacatc accgacgagc aaggcaagac cgatcgggcc    5820
c                                                                    5821

<210> SEQ ID NO 3
<211> LENGTH: 4949
<212> TYPE: DNA
<213> ORGANISM: Artificial sequence
<220> FEATURE:
<223> OTHER INFORMATION: Nucleic acid sequence of plasmid pMTL83155

<400> SEQUENCE: 3
cctgcaggat aaaaaattg tagataaatt ttataaaata gttttatcta caattttttt      60
atcaggaaac agctatgacc gcggccgcaa tatgatattt atgtccattg tgaaagggat    120
tatattcaac tattattcca gttacgttca tagaaatttt cctttctaaa atatttatt    180 ccatgtcaag aactctgttt atttcattaa agaactataa gtacaaagta taaggcattt    240
gaaaaaatag gctagtatat tgattgatta tttatttaa aatgcctaag tgaaatatat    300
acatattata acaataaaat aagtattagt gtaggatttt taaatagagt atctattttc    360
agattaaatt tttgattatt tgatttacat tatataatat tgagtaaagt attgactagc    420
aaaatttttt gatactttaa tttgtgaaat ttcttatcaa agttatatt tttgaataat    480 ttttattgaa aaatacaact aaaaaggatt atagtataag tgtgtgtaat tttgtgttaa    540
atttaaaggg aggaaatgaa catgaaacat atgaccatga ttacgaattc gagctcggta    600
cccggggatc ctctagagtc gacgtcacgc gtccatggag atctcgaggc ctgcagacat    660
gcaagcttgg cactggccgt cgttttacaa cgtcgtgact gggaaaaccc tggcgttacc    720
caacttaatc gccttgcagc acatccccct ttcgccagct ggcgtaatag cgaagaggcc    780
cgcaccgatc gcccttccca acagttgcgc agcctgaatg gcgaatggcg ctagcataaa    840
aataagaagc ctgcatttgc aggcttctta tttttatggc gcgccgccat tattttttg    900 aacaattgac aattcatttc ttattttta ttaagtgata gtcaaaaggc ataacagtgc    960
tgaatagaaa gaaatttaca gaaagaaaa ttatagaatt tagtatgatt aattatactc    1020
atttatgaat gtttaattga atacaaaaaa aaatacttgt tatgtattca attacgggtt    1080
aaaatataga caagttgaaa aatttaataa aaaataagt cctcagctct tatatattaa    1140
gctaccaact tagtatataa gccaaaactt aaatgtgcta ccaacacatc aagccgttag    1200
```

```
agaactctat ctatagcaat atttcaaatg taccgacata caagagaaac attaactata    1260
tatattcaat ttatgagatt atcttaacag atataaatgt aaattgcaat aagtaagatt    1320
tagaagttta tagcctttgt gtattggaag cagtacgcaa aggcttttt atttgataaa     1380 aattagaagt atatttattt tttcataatt aatttatgaa aatgaaaggg ggtgagcaaa    1440
gtgacagagg aaagcagtat cttatcaaat aacaaggtat tagcaatatc attattgact   1500
ttagcagtaa acattatgac ttttatagtg cttgtagcta agtagtacga aaggggagc    1560 tttaaaaagc tccttggaat acatagaatt cataaattaa tttatgaaaa gaagggcgta   1620
tatgaaaact tgtaaaaatt gcaaagagtt tattaaagat actgaaatat gcaaaataca   1680
ttcgttgatg attcatgata aaacagtagc aacctattgc agtaaataca atgagtcaag   1740
atgtttacat aaagggaaag tccaatgtat taattgttca aagatgaacc gatatggatg   1800
gtgtgccata aaaatgagat gttttacaga ggaagaacag aaaaaagaac gtacatgcat   1860
taaatattat gcaaggagct ttaaaaaagc tcatgtaaag aagagtaaaa agaaaaaata   1920
atttatttat taatttaata ttgagagtgc cgacacagta tgcactaaaa aatatatctg   1980
tggtgtagtg agccgataca aaaggatagt cactcgcatt ttcataatac atcttatgtt   2040
atgattatgt gtcggtggga cttcacgacg aaaacccaca ataaaaaaag agttcggggt   2100
agggttaagc atagttgagg caactaaaca atcaagctag gatatgcagt agcagaccgt   2160
aaggtcgttg tttaggtgtg ttgtaataca tacgctatta agatgtaaaa atacggatac   2220
caatgaaggg aaaagtataa ttttggatg tagtttgttt gttcatctat gggcaaacta    2280
cgtccaaagc cgtttccaaa tctgctaaaa agtatatcct ttctaaaatc aaagtcaagt   2340
atgaaatcat aaataaagtt taattttgaa gttattatga tattatgttt ttctattaaa   2400
ataaattaag tatatagaat agtttaataa tagtatatac ttaatgtgat aagtgtctga   2460
cagtgtcaca gaaaggatga ttgttatgga ttataagcgg ccggccagtg ggcaagttga   2520
aaaattcaca aaaatgtggt ataatatctt tgttcattag agcgataaac ttgaatttga   2580
gagggaactt agatggtatt tgaaaaaatt gataaaaata gttggaacag aaaagagtat   2640
tttgaccact actttgcaag tgtaccttgt acctacagca tgaccgttaa agtggatatc   2700
acacaaataa aggaaaaggg aatgaaaacta tatcctgcaa tgctttatta tattgcaatg   2760 attgtaaaacc gccattcaga gtttaggacg gcaatcaatc aagatggtga attgggata   2820 tatgatgaga tgataccaag ctatacaata tttcacaatg atactgaaac attttccagc   2880
ctttggactg agtgtaagtc tgactttaaa tcattttttag cagattatga aagtgatacg   2940
caacggtatg gaaacaatca tagaatggaa ggaaagccaa atgctccgga aaacatttttt   3000 aatgtatcta tgataccgtg gtcaaccttc gatggcttta atctgaattt gcagaaagga   3060
tatgattatt tgattcctat ttttactatg gggaaatatt ataaagaaga taacaaaatt   3120
atacttcctt tggcaattca agttcatcac gcagtatgtg acggatttca catttgccgt   3180
tttgtaaacg aattgcagga attgataaat agttaacttc aggtttgtct gtaactaaaa   3240
acaagtattt aagcaaaaac atcgtagaaa tacggtgttt tttgttaccc taagtttaaa   3300 ctccttttttg ataatctcat gaccaaaatc ccttaacgtg agttttcgtt ccactgagcg   3360
tcagaccccg tagaaaagat caaaggatct tcttgagatc cttttttttct gcgcgtaatc   3420 tgctgcttgc aaacaaaaaa accaccgcta ccagcggtgg tttgtttgcc ggatcaagag   3480
ctaccaactc tttttccgaa ggtaactggc ttcagcagag cgcagatacc aaatactgtt   3540
cttctagtgt agccgtagtt aggccaccac ttcaagaact ctgtagcacc gcctacatac   3600
```

| | |
|---|---|
| ctcgctctgc taatcctgtt accagtggct gctgccagtg gcgataagtc gtgtcttacc | 3660 |
| gggttggact caagacgata gttaccggat aaggcgcagc ggtcgggctg aacgggggt | 3720 |
| tcgtgcacac agcccagctt ggagcgaacg acctacaccg aactgagata cctacagcgt | 3780 |
| gagctatgag aaagcgccac gcttcccgaa gggagaaagg cggacaggta tccggtaagc | 3840 |
| ggcagggtcg gaacaggaga gcgcacgagg gagcttccag ggggaaacgc ctggtatctt | 3900 |
| tatagtcctg tcgggtttcg ccacctctga cttgagcgtc gattttgtg atgctcgtca | 3960 |
| gggggcgga gcctatggaa aaacgccagc aacgcggcct ttttacggtt cctggccttt | 4020 |
| tgctggcctt tgctcacat gttctttcct gcgttatccc ctgattctgt ggataaccgt | 4080 |
| attaccgcct ttgagtgagc tgataccgct cgccgcagcc gaacgaccga gcgcagcgag | 4140 |
| tcagtgagcg aggaagcgga agagcgccca atacgcaggg cccctgctt cggggtcatt | 4200 |
| atagcgattt tttcggtata tccatccttt ttcgcacgat atacaggatt ttgccaaagg | 4260 |
| gttcgtgtag actttccttg gtgtatccaa cggcgtcagc cggcaggat aggtgaagta | 4320 |
| ggcccacccg cgagcgggtg ttccttcttc actgtcectt attcgcacct ggcggtgctc | 4380 |
| aacgggaatc ctgctctgcg aggctggccg gctaccgccg gcgtaacaga tgagggcaag | 4440 |
| cggatggctg atgaaaccaa gccaaccagg aagggcagcc cacctatcaa ggtgtactgc | 4500 |
| cttccagacg aacgaagagc gattgaggaa aaggcggcgg cggccggcat gagcctgtcg | 4560 |
| gcctacctgc tggccgtcgg ccagggctac aaaatcacgg gcgtcgtgga ctatgagcac | 4620 |
| gtccgcgagc tggcccgcat caatggcgac ctgggccgcc tgggcggcct gctgaaactc | 4680 |
| tggctcaccg acgaccgcg cacggcgcgg ttcggtgatg ccacgatcct cgccctgctg | 4740 |
| gcgaagatcg aagagaagca ggacgagctt ggcaaggtca tgatgggcgt ggtccgcccg | 4800 |
| agggcagagc catgactttt ttagccgcta aaacggccgg ggggtgcgcg tgattgccaa | 4860 |
| gcacgtcccc atgcgctcca tcaagaagag cgacttcgcg gagctggtga agtacatcac | 4920 |
| cgacgagcaa ggcaagaccg atcgggccc | 4949 |

<210> SEQ ID NO 4
<211> LENGTH: 25
<212> TYPE: DNA
<213> ORGANISM: Artificial sequence
<220> FEATURE:
<223> OTHER INFORMATION: Synthetic primer

<400> SEQUENCE: 4
aagaagggcg tatatgaaaa cttgt         25

<210> SEQ ID NO 5
<211> LENGTH: 25
<212> TYPE: DNA
<213> ORGANISM: Artificial sequence
<220> FEATURE:
<223> OTHER INFORMATION: Synthetic primer

<400> SEQUENCE: 5
ttcgtttaca aaacggcaaa tgtga         25

<210> SEQ ID NO 6
<211> LENGTH: 37
<212> TYPE: DNA
<213> ORGANISM: Artificial sequence
<220> FEATURE:
<223> OTHER INFORMATION: Synthetic primer

```
<400> SEQUENCE: 6
ccgaattcgt cgacaacaga gtttgatcct ggctcag                              37

<210> SEQ ID NO 7
<211> LENGTH: 37
<212> TYPE: DNA
<213> ORGANISM: Artificial sequence
<220> FEATURE:
<223> OTHER INFORMATION: Synthetic primer

<400> SEQUENCE: 7
cccgggatcc aagcttacgg ctaccttgtt acgactt                              37

<210> SEQ ID NO 8
<211> LENGTH: 1207
<212> TYPE: DNA
<213> ORGANISM: Artificial sequence
<220> FEATURE:
<223> OTHER INFORMATION: 16s rRNA nucleic acid sequence of
      LZ-pMTL83155-1 obtained using primer rP2 (PCR product of plasmid)

<400> SEQUENCE: 8
cskmmtwwyr mwwkrammkt myyswawkrw mkkkrmkkss yggygttwac aaggcccggg     60
aacgtattca ccgcgacatt ctgattcgcg attactagca actccacttc atgtaggcga    120
gtttcagcct gcaatccgaa ctgggggcag tttttgaggt ttgctccacc ttgcggtctt    180
gcttctctct gtactgccca ttgtagcacg tgtgttgccc tggacataag gggcatgatg    240
atttgacgtc atccccacct tcctccgcgt taaccgcggc agtcttgcta gagtgctcaa    300
ctaaatgtta gcaactaaca cagggggttg sgctcgttgc aggacttaac ctaacatctc    360
acgacacgag ctgacgacaa ccatgcacca cctgtatccc tgccccgaag ggcttctctt    420
atctctaara tattcagggk atgtcaagtc caggwaaggt tsttcgcgtt gcttcsaatt    480
aaacmacatg ctccgctgct tgtgsgggcc sccstcaatt cctttgagtt ttaatcwtgc    540
gatcgtactt cccaggcgga gtactwattg tgtttactgc ggcacagaar aggkcgatam    600
ctcctacacc tartactcat cgtttacggc gtggastacc aggrtakcta atcctgtttg    660
ctacccacgc tttcgtgcct sakcrtcagt tacggtccas araatcgcct tcgccactgg    720
tgttsttyct aatstctacg cayytywycg ckacactarr aattmmattc tcctctcccg    780
crctctagat atccagttwg aaatgmastg mccgrgttaa gsssggsyat ttcacatctc    840
actyaatakc tgmctacgca ctctytacgc ccastaatyy ggacwksrct cgccyctacg    900
tattamyrwr rctgctggca cgtmgtagcg wgactsctsc ttgsgtacgt catatcgtcc    960
ycwmgacaga gcwkacatck aaacawcgtc acycmcscgc gtgctgcatc agywtmgmyc   1020
atstgcamaa tacmsacwgc tgcyccgtag agtytggaar grgkkycrat catkmrccga   1080
taccsktcca gwccgckryc caaygtgcct gtaggcgtac trcacgwgct atgcccgrga   1140
cactcacgga atcmcgtacg tcaggaactg aattwgggta tcattcggaw gccgtggrga   1200 rtacmgg                                                            1207

<210> SEQ ID NO 9
<211> LENGTH: 1179
<212> TYPE: DNA
<213> ORGANISM: Artificial sequence
<220> FEATURE:
<223> OTHER INFORMATION: 16s rRNA nucleic acid sequence of
      LZ-pMTL83155-2 obtained using primer rP2 (PCR product of plasmid)

<400> SEQUENCE: 9
```

-continued

```
tskkksyrrk syytgmrtrk rykswyawtk gcccgggaac wkattcaccg cgacattctg      60
attcgcgatt actagcaact ccaacttcat gtaggcgagt ttcagcctgc aatccgaact     120 ggggcagtt tttgaggttt gctccacctt gcggtcttgc ttctctctgt actgcccatt     180
gtagcacgtg tgttgccctg dacataaggg gcatgatgat ttgacgtcat ccccaccttc    240
ctccgcgtta accgcggcag tcttgctaga gtgctcaact aaatgttagc aactaacaac    300
aggggttgsg ctcgttgcag gacttaacct aacatctcac gacacgagct gacgacaacc    360
atgcaccacc tgtatccctg ccccgaaggg sttctcttat ctctaarata ttcagggtat    420
gtcaagtcca ggwaaggtts ttcgcgttgc ttckaattaa acmacatgct ccgctgcttg    480
tgsgggcscc cgtcaattcc tttgagtttt aatcwtgsga tcgtacttcc yasgsggagt    540
amttattgwg tttactgcgg cacagaaargr gkcgatacct cctacamcwa stactcrtcg   600
twtacggcgt ggaskaccag grtakmwaat cmtgtttgct acccacgctt tcktgccksa    660
kcrtcartta cggtccasar satcgcctwc gccactggtg ttsttyctaa trtctacgca    720
yctcaccgct rcactargaa wtmmawtctm ctcyccckcr skmkaratat mcasttwgwa    780
awrmarygms sgggttrwgs rsggssryyt cayatctcam ttaaatatst gmctacscac    840
kcmytmcgcs caryaattyy kgacwgmrcr mgccycsyac gtattaywww agmtgmwrgc    900
mcgymgktag cggwgwrkrc mtcckyktgg tasccktsaty atcgtcyccw mgammarrsw   960
kwryawwstt aacmtmstma mtccsyawcg ttgstgrtca gtgcttwswy atstgcacaa   1020
twcwrmmwgm tgcyccgtas agtytggamr trttgaawca tywrcctats rcgckycagt  1080
cggkcacacg tgcttgawkg cgttrctkac rcmgtcaacg mctgagcakc acgrgcctga  1140
ggakcmgtca accgmtatgg gatrgatatt mggtatccg                          1179
```

<210> SEQ ID NO 10
<211> LENGTH: 1159
<212> TYPE: DNA
<213> ORGANISM: Artificial sequence
<220> FEATURE:
<223> OTHER INFORMATION: 16s rRNA nucleic acid sequence of
      LZ-pMTL83155-hs-tk-1 obtained using primer rP2 (PCR product of
      plasmid)

<400> SEQUENCE: 10

```
ggktwttggg ccamtkytwc tcattggtrk kgacgggcgg tgtgtacaag gcccgggaac     60
gtattcaccg cgacattctg attcgcgatt actagcaact ccaacttcat gtaggcgagt   120
ttcagcctgc aatccgaact ggggcagtt tttgaggttt gctccacctt gcggtcttgc   180
ttctctctgt actgcccatt gtagcacgtg tgttgccctg dacataaggg gcatgatgat   240
ttgacgtcat ccccaccttc ctccgcgtta accgcggcag tcttgctaga gtgctcaact   300
aaatgttagc aactaacaac aggggttgcg ctcgttgcag gacttaacct aacatctcac   360
gacacgagct gacgacaacc atgcaccacc tgtatccctg ccccgaaggg yttctcttat   420
ctctaagata ttcagggtat gtcaagtcca ggtaaggttc ttcgcgttgc ttcgaattaa   480
acmacatgct ccgctgcttg tgcgggcccc cgtcaattcc tttgagtttt aatcttgcga   540
tcgtacttcc caggcggagt acttattgtg tttactgcgg cacagaaagg gtcgatacct   600
cctacaccta gtactcatcg tttacggcgt ggastaccag ggtatctaat cmtgtttgct   660
acccacgctt tcgtgcctca gcgtcagtta cggtccasag aatcgccttc gccactggtg   720
ttsttcctaa tctctacgca yttcaccgct acactaggaa ttccattctc ctctcccgca   780
```

| ctctagatat | ccagtttgaa | atgcagtgcc | sgggttaagc | cggsgtattt | cacatctcac | 840 |
| ttaaatatcy | gcctacgcac | tctttacgcc | cagtaatycg | gacasgctcg | ccacctacgt | 900 |
| attaccgcrg | ctgctggcac | gtagktagcg | kgctkctctt | ggtacgtcat | tatcgtccca | 960 |
| agacagagct | tacatckaaa | ctctcactcm | gcgcgttgct | gcatcagytt | cgycatgtgc | 1020 |
| atatcscact | gctgcyccgt | agagkytgga | cggwsyycat | tcatgtgcga | tmccktcagt | 1080 |
| cgctasccat | cgygcctgtr | gsttacctac | cackagctaw | rsscccgrgt | cmcycycaac | 1140 |
| ggatayccgt | kaawcgtcg | | | | | 1159 |

<210> SEQ ID NO 11
<211> LENGTH: 1188
<212> TYPE: DNA
<213> ORGANISM: Artificial sequence
<220> FEATURE:
<223> OTHER INFORMATION: 16s rRNA nucleic acid sequence of
      LZ-pMTL83155-hs-tk-2 obtained using primer rP2 (PCR product of
      plasmid)

<400> SEQUENCE: 11

| crcwcwycky | rttwwtwmwt | wwggtkktga | cgggcggtgt | gtacaaggcc | cgggaacgta | 60 |
| ttcaccgcga | cattctgatt | cgcgattact | agcaactcca | acttcatgta | ggcgagtttc | 120 |
| agcctgcaat | ccgaactggg | ggcagttttt | gaggtttgct | ccaccttgcg | gtcttgcttc | 180 |
| tctctgtact | gcccattgta | gcacgtgtgt | tgccctggac | ataaggggca | tgatgatttg | 240 |
| acgtcatccc | caccttcctc | cgcgttaacc | gcggcagtct | tgctagagtg | ctcaactaaa | 300 |
| tgttagcaac | taacaacagg | ggttgcgctc | gttgcaggac | ttaacctaac | atctcacgac | 360 |
| acgagctgac | gacaaccatg | caccacctgt | atccctgccc | gaagggytt | ctcttatctc | 420 |
| taagatattc | agggtatgtc | aagtccaggt | aaggttcttc | gcgttgcttc | gaattaaacc | 480 |
| acatgctccg | ctgcttgtgc | gggccccgt | caattccttt | gagttttaat | cttgcgatcg | 540 |
| tacttcccag | gcggagtact | tattgtgttt | actgcggcac | agaaggggtc | gatacctcct | 600 |
| acacctagta | ctcatcgttt | acggcgtgga | ctaccagggt | atctaatcct | gtttgctacc | 660 |
| cacgctttcg | tgcctcagcg | tcagttacgg | tccagagaat | cgccttcgcc | actggtgttc | 720 |
| ttcctaatct | ctacgcattt | caccgctaca | ctaggaattc | cattctcctc | tcccgcactc | 780 |
| tagatatcca | gtttgaaatg | cagtgccgg | gttaagcccg | gtatttcac | atctcactta | 840 |
| aatatccgcc | tacgcactct | ttacgcccag | taattccgga | caacgctcgc | cacctacgta | 900 |
| ttaccgcggc | tgctggcacg | tagttagccg | tgcttctcct | tggtacgtca | tatcgtccca | 960 |
| agamgagctt | acatccgaaa | ctctcactcm | gcgcgtgctg | catcagcttc | gccatgtgca | 1020 |
| tatcccactg | ctgcyccgta | gagtctgacg | tyyycatcaa | tgtgcgatcm | cctctcagtc | 1080 |
| gcwmscatcg | tsctgtagcg | tacctacacw | gctatggccg | gtcmycycag | cgawtccgta | 1140 |
| tmgycatgaa | cygatatatg | cgatkattcc | cttcggagca | tccccctg | | 1188 |

<210> SEQ ID NO 12
<211> LENGTH: 1032
<212> TYPE: DNA
<213> ORGANISM: Clostridium autoethanogenum

<400> SEQUENCE: 12

| gtgaaaggag | agtttaaaat | gaaagaagaa | ttaaaacaga | taaggaaaa | tgcctttaac | 60 |
| gaattaaaaa | ataaaaagtt | agatatagag | gatataagag | ttaatatttt | aggtaaaaag | 120 |
| ggagaactta | caaaaatact | caggggcatg | aaggatcttt | ccaaagaaga | aagacctgca | 180 |

```
attggtaagc ttgccaatga agtgaggagt acactggaaa atgctataga agaggcatca    240
aaaaagataa aatcaagtgc tatacaagca aagctgcaga atgaaacaat tgatattact    300
atgcctggca taaagcaaac tgtaggaaag cgccatccgc tagaacaaac actagaagag    360
atgaaacaga tatttatttc tatgggattt actatagaag aaggtcctga agtagagaag    420
gattattata actttgaagc acttaacata cctaaaaatc atccagcaag gggtgaacag    480 gataccttt atataaatga caatgtagtg cttagaactc aaacttctcc aatacaggta    540
agaactatgg aaaaacaaaa accccccaata aagatgatat ctccaggtaa agtttatcgt    600
tcagattcag tggatgctac tcattcacct atattttatc aaatggaagg cctagtagtt    660
gacaaaggta taacttttgc aaatttaaaa ggcactcttg aactatttgc taaaaagtta    720
ttcggaaatg acatacgtac aaaattcaga cctcatcatt tccctttac agaaccttct    780 gcagaaatgg atgccagttg ctttgtatgc catggaaaag gctgcagagt atgtaaggga    840
gaagggtgga tagaactttt aggatgcgga atggttcatc ctcaggtact agaaaattgt    900
ggaatagatc ctgaagttta tagtggattt gcttttggaa tgggtgtaga taggatggtc    960
atgttaaaat acggaataga tgatataaga aacatgtatg aaagtgacat gagattttta    1020
aatcaatttt aa                                                         1032

<210> SEQ ID NO 13
<211> LENGTH: 984
<212> TYPE: DNA
<213> ORGANISM: Eschericia coli

<400> SEQUENCE: 13
atgtcacatc tcgcagaact ggttgccagt gcgaaggcgg ccattagcca ggcgtcagat     60
gttgccgcgt tagataatgt gcgcgtcgaa tatttgggta aaaaagggca cttaacccct    120
cagatgacga ccctgcgtga gctgccgcca aagagcgtc cggcagctgg tgcggttatc    180
aacgaagcga aagagcaggt tcagcaggcg ctgaatgcgc gtaaagcgga actggaaagc    240
gctgcactga atgcgcgtct ggcggcggaa acgattgatg tctctctgcc aggtcgtcgc    300
attgaaaacg gcggtctgca tccggttacc cgtaccatcg accgtatcga agtttcttc    360 ggtgagcttg gctttaccgt ggcaaccggg ccggaaatcg aagacgatta tcataacttc    420
gatgctctga acattcctgg tcaccacccg gcgcgcgctg accacgacac tttctggttt    480
gacactaccc gcctgctgcg tacccagacc tctggcgtac agatccgcac catgaaagcc    540
cagcagccac cgattcgtat catcgcgcct ggccgtgttt atcgtaacga ctacgaccag    600
actcacacgc cgatgttcca tcagatggaa ggtctgattg ttgataccaa catcagcttt    660
accaacctga aggcacgct gcacgacttc ctgcgtaact ctctttgagga agatttgcag    720 attcgcttcc gtccttccta cttcccgttt accgaacctt ctgcagaagt ggacgtcatg    780
ggtaaaaacg gtaaatggct ggaagtgctg ggctgcggga tggtgcatcc gaacgtgttg    840
cgtaacgttg gcatcgaccc ggaagtttac tctggtttcg ccttcgggat ggggatggag    900
cgtctgacta tgttgcgtta cggcgtcacc gacctgcgtt cattcttcga aaacgatctg    960
cgtttcctca aacagtttaa ataa                                            984

<210> SEQ ID NO 14
<211> LENGTH: 1040
<212> TYPE: DNA
<213> ORGANISM: Clostridium autoethanogenum
```

<400> SEQUENCE: 14

```
gtgaaaggag agtttaaaat gaaagaagaa ttaaaacaga taaaggaaaa tgcctttaac      60
gaattaaaaa ataaaaagtt agatatagag gatataagag ttaaatattt aggtaaaaag     120
ggagaactta caaaaatact caggggcatg aaggatcttt ccaaagaaga aagacctgca     180
attggtaagc ttgccaatga agtgaggagt acactggaaa atgctataga agaggcatca     240
aaaaagataa aatcaagtgc tatacaagca aagctgcaga atgaaacaat tgatattact     300
atgcctggca taaagcaaac tgtaggaaag cgccatccgc tagaacaaac actagaagag     360
atgaaacaga tatttatttc tatgggattt actatagaag aaggtcctga agtagagaag     420
gattattata actttgaagc acttaacata cctaaaaatc atccagcaag gggtgaacag     480
gataccttt atataaatga caatgtagtg cttagaactc aaacttctcc aatacaggta      540
agaactatgg aaaaacaaaa acccccaata aagatgatat ctccaggtaa agtttatcgt     600
tcagattcag tggatgctac tcattcacct atattttatc aaatggaagg cctagtagtt     660
gacaaaggta taacttttgc aaatttaaaa ggcactcttg aactatttgc taaaaagtta     720
ttcggaaatg acatacgtac aaaattcaga cctcatcatt tcccttttac agaaccttct     780
gcagaaatgg atgccagttg ctttgtatgc catggaaaag gctgcagagt atgtaaggga     840
gaagggtgga tagaactttt aggatgcgga atggttcatc ctcaggtact agaaattgt      900
ggaatagatc ctgaagttta tagtggattt ggttttggaa tgggtgtaga taggatggtc     960
atgttaaaat acggaataga tgatataaga acatgtatg aaagtgacat gagatttta     1020
aatcaatttt aagtttaaac                                                1040
```

<210> SEQ ID NO 15
<211> LENGTH: 18
<212> TYPE: DNA
<213> ORGANISM: Artificial sequence
<220> FEATURE:
<223> OTHER INFORMATION: Synthetic primer

<400> SEQUENCE: 15

```
actggccgtc gttttaca                                                     18
```

<210> SEQ ID NO 16
<211> LENGTH: 18
<212> TYPE: DNA
<213> ORGANISM: Artificial sequence
<220> FEATURE:
<223> OTHER INFORMATION: Synthetic primer

<400> SEQUENCE: 16

```
caggaaacag ctatgacc                                                     18
```

<210> SEQ ID NO 17
<211> LENGTH: 73
<212> TYPE: DNA
<213> ORGANISM: Artificial sequence
<220> FEATURE:
<223> OTHER INFORMATION: Synthetic promoter PpheS*

<400> SEQUENCE: 17

```
gtttaaacct ctatattgac aaaaataata atagtgggta taattaagtt gttatagaaa      60
ggaggatgta tag                                                         73
```

<210> SEQ ID NO 18
<211> LENGTH: 4835

```
<212> TYPE: DNA
<213> ORGANISM: Artificial sequence
<220> FEATURE:
<223> OTHER INFORMATION: Plasmid pMTL85151-pheS*

<400> SEQUENCE: 18
atgaagtgag gagtacactg gaaaatgcta tagaagaggc atcaaaaaag ataaaatcaa    60
gtgctataca agcaaagctg cagaatgaaa caattgatat tactatgcct ggcataaagc   120
aaactgtagg aaagcgccat ccgctagaac aaacactaga agagatgaaa cagatattta   180
tttctatggg atttactata gaagaaggtc ctgaagtaga aaggattat tataactttg    240
aagcacttaa catacctaaa atcatccag caagggg tga acaggatacc ttttatataa    300
atgacaatgt agtgcttaga actcaaactt ctccaataca ggtaagaact atggaaaaac   360
aaaaaccccc aataaagatg atatctccag gtaaagttta tcgttcagat tcagtggatg   420
ctactcattc acctatattt tatcaaatgg aaggcctagt agttgacaaa ggtataactt   480
ttgcaaattt aaaaggcact cttgaactat ttgctaaaaa gttattcgga atgacatac    540
gtacaaaatt cagacctcat catttcccctt ttacagaacc ttctgcagaa atggatgcca   600
gttgctttgt atgccatgga aaaggctgca gagtatgtaa gggagaaggg tggatagaac   660
ttttaggatg cggaatggtt catcctcagg tacttagaaa ttgtggaata gatcctgaag   720
tttatagtgg atttggtttt ggaatgggtg tagatagga ggtcatgtta aaatacggaa    780
tagatgatat aagaaacatg tatgaaagtg acatgagatt tttaaatcaa tttttaagttt   840
aaactccttt ttgataatct catgaccaaa atcccttaac gtgagttttc gttccactga   900
gcgtcagacc ccgtagaaaa gatcaaagga tcttcttgag atcctttttt tctgcgcgta   960
atctgctgct tgcaaacaaa aaaaccaccg ctaccagcgg tggtttgttt gccggatcaa  1020
gagctaccaa ctcttttttcc gaaggtaact ggcttcagca gagcgcagat accaaatact  1080
gtccttctag tgtagccgta gttaggccac cacttcaaga actctgtagc accgcctaca  1140
tacctcgctc tgctaatcct gttaccagtg gctgctgcca gtggcgataa gtcgtgtctt  1200
accgggttgg actcaagacg atagttaccg gataaggcgc agcggtcggg ctgaacgggg  1260
ggttcgtgca cacagcccag cttggagcga acgacctaca ccgaactgag atacctacag  1320
cgtgagcatt gagaaagcgc cacgcttccc gaagggagaa aggcggacag gtatccggta  1380
agcggcaggg tcggaacagg agagcgcacg agggagcttc caggggggaaa cgcctggtat  1440
ctttatagtc ctgtcgggtt tcgccacctc tgacttgagc gtcgattttt gtgatgctcg  1500
tcagggggggc ggagcctatg gaaaaacgcc agcaacgcgg cctttttacg gttcctggcc  1560
ttttgctggc cttttgctca catgttcttt cctgcgttat cccctgattc tgtggataac  1620
cgtattaccg cctttgagtg agctgatacc gctcgccgca gccgaacgac cgagcgcagc  1680
gagtcagtga gcgaggaagc ggaagagcgc ccaatacgca gggcccccctg cttcggggtc  1740
attatagcga ttttttcggt atatccatcc tttttcgcac gatatacagg attttgccaa  1800
agggttcgtg tagactttcc ttggtgtatc caacggcgtc agccgggcag gataggtgaa  1860
gtaggcccac ccgcgagcgg gtgttccttc ttcactgtcc cttattcgca cctggcggtg  1920
ctcaacggga atcctgctct gcgaggctgg ccggctaccg ccggcgtaac agatgagggc  1980
aagcggatgg ctgatgaaac caagccaacc aggaagggca gcccacctat caaggtgtac  2040
tgccttccag acgaacgaag agcgattgag gaaaaggcgg cggcggccgg catgagcctg  2100
tcggcctacc tgctggccgt cggccagggc tacaaaatca cgggcgtcgt ggactatgag  2160
```

```
cacgtccgcg agctggcccg catcaatggc gacctgggcc gcctgggcgg cctgctgaaa    2220
ctctggctca ccgacgaccc gcgcacggcg cggttcggtg atgccacgat cctcgccctg    2280
ctggcgaaga tcgaagagaa gcaggacgag cttggcaagg tcatgatggg cgtggtccgc    2340
ccgagggcag agccatgact tttttagccg ctaaaacggc cggggggtgc gcgtgattgc    2400
caagcacgtc cccatgcgct ccatcaagaa gagcgacttc gcggagctgg tgaagtacat    2460
caccgacgag caaggcaaga ccgatcgggc cccctgcagg ataaaaaaat tgtagataaa    2520
ttttataaaa tagttttatc tacaattttt ttatcaggaa acagctatga ccgcggccgc    2580
tgtatccata tgaccatgat tacgaattcg agctcggtac ccggggatcc tctagagtcg    2640
acgtcacgcg tccatggaga tctcgaggcc tgcagacatg caagcttggc actgccgtc    2700 gttttacaac gtcgtgactg gaaaaccct ggcgttaccc aacttaatcg ccttgcagca    2760
catccccctt tcgccagctg gcgtaatagc gaagaggccc gcaccgatcg cccttcccaa    2820
cagttgcgca gcctgaatgg cgaatggcgc tagcataaaa ataagaagcc tgcatttgca    2880
ggcttcttat ttttatggcg cgccgcattc acttcttttc tatataaata tgagcgaagc    2940
gaataagcgt cggaaaagca gcaaaaagtt ccttttttgc tgttggagca tgggggttca    3000
gggggtgcag tatctgacgt caatgccgag cgaaagcgag ccgaagggta gcatttacgt    3060
tagataaccc cctgatatgc tccgacgctt tatatagaaa agaagattca actaggtaaa    3120
atcttaatat aggttgagat gataaggttt taaggaatt tgtttgttct aatttttcac    3180 tcatttgtt ctaatttctt ttaacaaatg ttcttttttt tttagaacag ttatgatata    3240
gttagaatag tttaaaataa ggagtgagaa aaagatgaaa gaaagatatg gaacagtcta    3300
taaaggctct cagaggctca tagacgaaga aagtggagaa gtcatagagg tagacaagtt    3360
ataccgtaaa caaacgtctg gtaacttcgt aaaggcatat atagtgcaat taataagtat    3420
gttagatatg attggcggaa aaaaacttaa aatcgttaac tatatcctag ataatgtcca    3480
cttaagtaac aatacaatga tagctacaac aagagaaata gcaaaagcta caggaacaag    3540
tctacaaaca gtaataacaa cacttaaaat cttagaagaa ggaaatatta taaaagaaa    3600 aactggagta ttaatgttaa accctgaact actaatgaga ggcgacgacc aaaaacaaaa    3660
atacctctta ctcgaatttg ggaactttga gcaagaggca aatgaaatag attgacctcc    3720
caataacacc acgtagttat tgggaggtca atctatgaaa tgcgattaag ggccggccaa    3780
gtgggcaagt tgaaaaattc acaaaaatgt ggtataatat ctttgttcat tagagcgata    3840
aacttgaatt tgagagggaa cttagatggt atttgaaaaa attgataaaa atagttggaa    3900
cagaaaagag tattttgacc actactttgc aagtgtacct tgtacctaca gcatgaccgt    3960
taaagtggat atcacacaaa taaggaaaa gggaatgaaa ctatatcctg caatgcttta    4020
ttatattgca atgattgtaa accgccattc agagtttagg acggcaatca atcaagatgg    4080
tgaattgggg atatatgatg agatgatacc aagctataca atatttcaca atgatactga    4140
aacattttcc agcctttgga ctgagtgtaa gtctgacttt aaatcatttt tagcagatta    4200
tgaaagtgat acgcaacggt atggaaacaa tcatagaatg gaaggaaagc caaatgctcc    4260
ggaaaacatt tttaatgtat ctatgatacc gtggtcaacc ttcgatggct taatctgaa    4320 tttgcagaaa ggatatgatt atttgattcc tattttact atggggaaat attataaaga    4380
agataacaaa attatacttc ctttggcaat tcaagttcat cacgcagtat gtgacggatt    4440
tcacatttgc cgttttgtaa acgaattgca ggaattgata aatagttaac ttcaggtttg    4500
tctgtaacta aaaacaagta tttaagcaaa aacatcgtag aaatacggtg ttttttgtta    4560
```

```
cctaagttt aaacctctat attgacaaaa ataataatag tgggtataat taagttgtta    4620
tagaaaggag gatgtatagg tgaaaggaga gtttaaaatg aaagaagaat taaaacagat    4680
aaaggaaaat gcctttaacg aattaaaaaa taaaaagtta gatatagagg atataagagt    4740
taaatattta ggtaaaaagg gagaacttac aaaaatactc aggggcatga aggatctttc    4800
caaagaagaa agacctgcaa ttggtaagct tgcca                              4835
```

<210> SEQ ID NO 19
<211> LENGTH: 1131
<212> TYPE: DNA
<213> ORGANISM: Herpes simplex

<400> SEQUENCE: 19

```
atggcttcgt accCctgcca tcaacacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg ccctgggtt cgcgcgacga tatcgtctac      240
gtacccgagc cgatgactta ctggcgggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccggccct caccctcatc      480 ttcgaccgcc atcccatcgc cgccctcctg tgctacccgg ccgcgcggta ccttatgggc     540
agcatgaccc cccaggccgt gctggcgttc gtggccctca tcccgccgac cttgcccggc     600
acaaacatcg tgttggggc ccttccggag acagacaca tcgaccgcct ggccaaacgc      660
cagcgccccg gtgagcggct tgacctggct atgctggccg cgattcgccg cgtttacggg     720
ctacttgcca atacggtgcg gtatctgcag tgcggcgggt cgtggcggga ggattgggga     780
cagctttcgg gagcggcctt gacgccccag ggtgccgagc cccagagcaa cgcgggccca     840 cgacccata tcggggaaac gttatttacc ctgtttcggg cccccgagtt gctggccccc     900
aacggcgacc tgtacaacgt gtttgcctgg gccttggacg tcttggccaa cgcctccgt     960 cccatgcacg tctttatcct ggattacgac caatcgcccg ccggctgccg ggacgccctg    1020
ctgcaactta cctccgggat ggtccagacc catgtcacca ccccaggctc cataccgacg    1080
atctgcgacc tggcgcgcac gtttgcccgg gagatggggg aggctcactg a             1131
```

<210> SEQ ID NO 20
<211> LENGTH: 327
<212> TYPE: PRT
<213> ORGANISM: Eschericia coli

<400> SEQUENCE: 20

```
Met Ser His Leu Ala Glu Leu Val Ala Ser Ala Lys Ala Ala Ile Ser
1               5                   10                  15

Gln Ala Ser Asp Val Ala Ala Leu Asp Asn Val Arg Val Glu Tyr Leu
            20                  25                  30

Gly Lys Lys Gly His Leu Thr Leu Gln Met Thr Thr Leu Arg Glu Leu
        35                  40                  45

Pro Pro Glu Glu Arg Pro Ala Ala Gly Ala Val Ile Asn Glu Ala Lys
    50                  55                  60

Glu Gln Val Gln Gln Ala Leu Asn Ala Arg Lys Ala Glu Leu Glu Ser
65                  70                  75                  80
```

```
Ala Ala Leu Asn Ala Arg Leu Ala Ala Glu Thr Ile Asp Val Ser Leu
                85                  90                  95

Pro Gly Arg Arg Ile Glu Asn Gly Gly Leu His Pro Val Thr Arg Thr
            100                 105                 110

Ile Asp Arg Ile Glu Ser Phe Phe Gly Glu Leu Gly Phe Thr Val Ala
        115                 120                 125

Thr Gly Pro Glu Ile Glu Asp Asp Tyr His Asn Phe Asp Ala Leu Asn
    130                 135                 140

Ile Pro Gly His His Pro Ala Arg Ala Asp His Asp Thr Phe Trp Phe
145                 150                 155                 160

Asp Thr Thr Arg Leu Leu Arg Thr Gln Thr Ser Gly Val Gln Ile Arg
                165                 170                 175

Thr Met Lys Ala Gln Gln Pro Pro Ile Arg Ile Ile Ala Pro Gly Arg
            180                 185                 190

Val Tyr Arg Asn Asp Tyr Asp Gln Thr His Thr Pro Met Phe His Gln
        195                 200                 205

Met Glu Gly Leu Ile Val Asp Thr Asn Ile Ser Phe Thr Asn Leu Lys
    210                 215                 220

Gly Thr Leu His Asp Phe Leu Arg Asn Phe Phe Glu Glu Asp Leu Gln
225                 230                 235                 240

Ile Arg Phe Arg Pro Ser Tyr Phe Pro Phe Thr Glu Pro Ser Ala Glu
                245                 250                 255

Val Asp Val Met Gly Lys Asn Gly Lys Trp Leu Glu Val Leu Gly Cys
            260                 265                 270

Gly Met Val His Pro Asn Val Leu Arg Asn Val Gly Ile Asp Pro Glu
        275                 280                 285

Val Tyr Ser Gly Phe Ala Phe Gly Met Gly Met Glu Arg Leu Thr Met
    290                 295                 300

Leu Arg Tyr Gly Val Thr Asp Leu Arg Ser Phe Phe Glu Asn Asp Leu
305                 310                 315                 320

Arg Phe Leu Lys Gln Phe Lys
                325
```

<210> SEQ ID NO 21
<211> LENGTH: 343
<212> TYPE: PRT
<213> ORGANISM: Clostridium autoethanogenum

<400> SEQUENCE: 21

```
Val Lys Gly Glu Phe Lys Met Lys Glu Glu Leu Lys Gln Ile Lys Glu
1               5                   10                  15

Asn Ala Phe Asn Glu Leu Lys Asn Lys Lys Leu Asp Ile Glu Asp Ile
            20                  25                  30

Arg Val Lys Tyr Leu Gly Lys Lys Gly Glu Leu Thr Lys Ile Leu Arg
        35                  40                  45

Gly Met Lys Asp Leu Ser Lys Glu Glu Arg Pro Ala Ile Gly Lys Leu
    50                  55                  60

Ala Asn Glu Val Arg Ser Thr Leu Glu Asn Ala Ile Glu Glu Ala Ser
65                  70                  75                  80

Lys Lys Ile Lys Ser Ser Ala Ile Gln Ala Lys Leu Gln Asn Glu Thr
                85                  90                  95

Ile Asp Ile Thr Met Pro Gly Ile Lys Gln Thr Val Gly Lys Arg His
            100                 105                 110

Pro Leu Glu Gln Thr Leu Glu Glu Met Lys Gln Ile Phe Ile Ser Met
```

```
                    115                 120                 125
        Gly Phe Thr Ile Glu Glu Gly Pro Glu Val Glu Lys Asp Tyr Tyr Asn
            130                 135                 140

Phe Glu Ala Leu Asn Ile Pro Lys Asn His Pro Ala Arg Gly Glu Gln
        145                 150                 155                 160

Asp Thr Phe Tyr Ile Asn Asp Asn Val Val Leu Arg Thr Gln Thr Ser
                        165                 170                 175

Pro Ile Gln Val Arg Thr Met Glu Lys Gln Lys Pro Pro Ile Lys Met
                    180                 185                 190

Ile Ser Pro Gly Lys Val Tyr Arg Ser Asp Ser Val Asp Ala Thr His
                195                 200                 205

Ser Pro Ile Phe Tyr Gln Met Glu Gly Leu Val Val Asp Lys Gly Ile
            210                 215                 220

Thr Phe Ala Asn Leu Lys Gly Thr Leu Glu Leu Phe Ala Lys Lys Leu
        225                 230                 235                 240

Phe Gly Asn Asp Ile Arg Thr Lys Phe Arg Pro His His Phe Pro Phe
                        245                 250                 255

Thr Glu Pro Ser Ala Glu Met Asp Ala Ser Cys Phe Val Cys His Gly
                    260                 265                 270

Lys Gly Cys Arg Val Cys Lys Gly Glu Gly Trp Ile Glu Leu Leu Gly
                275                 280                 285

Cys Gly Met Val His Pro Gln Val Leu Arg Asn Cys Gly Ile Asp Pro
            290                 295                 300

Glu Val Tyr Ser Gly Phe Ala Phe Gly Met Gly Val Asp Arg Met Val
        305                 310                 315                 320

Met Leu Lys Tyr Gly Ile Asp Ile Arg Asn Met Tyr Glu Ser Asp
                        325                 330                 335

Met Arg Phe Leu Asn Gln Phe
                    340

<210> SEQ ID NO 22
<211> LENGTH: 1131
<212> TYPE: DNA
<213> ORGANISM: Herpes simplex

<400> SEQUENCE: 22
atggcttcgt accoctgcca tcaacacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagcggtcc ccacgggatg      180 gggaaaacca ccaccacgca actgctggtg gccctgggtt cgcgcgacga tatcgtctac     240
gtacccgagc cgatgactta ctggcgggtg ctggggctt ccgagacaat cgcgaacatc      300
tacaccacac aacaccgcct cgaccagggt gagatatcgg ccggggacgc ggcggtggta     360
atgacaagcg cccagataac aatgggcatg cctatgccg tgaccgacgc cgttctggct      420
cctcatatcg gggggaggc tgggagctca catgccccgc cccggccct caccctcatc       480 ttcgaccgcc atcccatcgc cgccctcctg tgctacccgg ccgcgcggta ccttatgggc     540
agcatgaccc ccaggccgt gctggcgttc gtggccctca tcccgccgac cttgcccggc     600
acaaacatcg tgttggggc ccttccggag acagacaca tcgaccgcct ggccaaacgc       660
cagcgccccg gtgagcggct tgacctggct atgctggccg cgattcgccg cgtttacggg     720
ctacttgcca atacggtgcg gtatctgcag tgccgcgggt cgtggcggga ggattgggga     780
cagctttcgg gagcggcctt gacgccccag ggtgccgagc cccagagcaa cgcgggccca     840
```
cgaccccata tcggggaaac gttatttacc ctgtttcggg cccccgagtt gctggccccc 900
aacggcgacc tgtacaacgt gtttgcctgg gccttggacg tcttggccaa acgcctccgt 960
cccatgcacg tctttatcct ggattacgac caatcgcccg ccggctgccg ggacgccctg 1020
ctgcaactta cctccgggat ggtccagacc catgtcacca ccccaggctc cataccgacg 1080
atctgcgacc tggcgcgcac gtttgcccgg gagatggggg aggctcactg a 1131

<210> SEQ ID NO 23
<211> LENGTH: 621
<212> TYPE: DNA
<213> ORGANISM: Clostridium perfringens

<400> SEQUENCE: 23
atggtatttg aaaaaattga taaaaatagt tggaacagaa aagagtattt tgaccactac 60
tttgcaagtg taccttgtac ctacagcatg accgttaaag tggatatcac acaaataaag 120
gaaaagggaa tgaaactata tcctgcaatg ctttattata ttgcaatgat tgtaaaccgc 180
cattcagagt ttaggacggc aatcaatcaa gatggtgaat tggggatata tgatgagatg 240
ataccaagct atacaatatt tcacaatgat actgaaacat tttccagcct ttggactgag 300
tgtaagtctg actttaaatc atttttagca gattatgaaa gtgatacgca acggtatgga 360
aacaatcata gaatggaagg aaagccaaat gctccggaaa acatttttaa tgtatctatg 420
ataccgtggt caaccttcga tggctttaat ctgaatttgc agaaaggata tgattatttg 480
attcctattt ttactatggg gaaatattat aaagaagata acaaaattat acttcctttg 540
gcaattcaag ttcatcacgc agtatgtgac ggatttcaca tttgccgttt tgtaaacgaa 600
ttgcaggaat tgataaatag t 621

<210> SEQ ID NO 24
<211> LENGTH: 738
<212> TYPE: DNA
<213> ORGANISM: Peptoclostridium difficile

<400> SEQUENCE: 24
atgaacaaaa atataaaata ttctcaaaac tttttaacga gtgaaaaagt actcaaccaa 60
ataataaaac aattgaattt aaaagaaacc gataccgttt acgaaattgg aacaggtaaa 120
gggcatttaa cgacgaaact ggctaaaata agtaaacagg taacgtctat tgaattagac 180
agtcatctat tcaacttatc gtcagaaaaa ttaaaactga atactcgtgt cactttaatt 240
caccaagata ttctacagtt tcaattccct aacaaacaga ggtataaaat tgttgggagt 300
attccttacc atttaagcac acaaattatt aaaaaagtgg tttttgaaag ccatgcgtct 360
gacatctatc tgattgttga agaaggattc tacaagcgta ccttggatat tcaccgaaca 420
ctagggttgc tcttgcacac tcaagtctcg attcagcaat tgcttaagct gccagcggaa 480
tgctttcatc ctaaaccaaa agtaaacagt gtcttaataa aacttacccg ccataccaca 540
gatgttccag ataaatattg gaagctatat acgtactttg tttcaaaatg ggtcaatcga 600
gaatatcgtc aactgtttac taaaaatcag tttcatcaag caatgaaaca cgccaaagta 660
aacaatttaa gtaccgttac ttatgagcaa gtattgtcta tttttaatag ttatctatta 720
tttaacggga ggaaataa 738

<210> SEQ ID NO 25
<211> LENGTH: 1275
<212> TYPE: DNA

<213> ORGANISM: Escherichia coli

<400> SEQUENCE: 25

```
atgtccacca acttatcagt gataaagaat ccgcgcgttc aatcggacca gcggaggctg      60
gtccggaggc cagacgtgaa acccaacaga cccctgatcg taattctgag cactgtcgcg     120
ctcgacgctg tcggcatcgg cctgattatg ccggtgctgc cgggcctcct gcgcgatctg     180
gttcactcga acgacgtcac cgcccactat ggcattctgc tggcgctgta tgcgttgatg     240
caatttgcct gcgcacctgt gctgggcgcg ctgtcggatc gtttcgggcg gcggccggtc     300
ttgctcgtct cgctggccgg cgctgctgtc gactacgcca tcatggcgac ggcgcctttc     360
ctttgggttc tctatatcgg gcggatcgtg gccggcatca ccggggcgac tggggcggta     420
gccggcgctt atattgccga tatcactgat ggcgatgagc gcgcgcggca cttcggcttc     480
atgagcgcct gtttcgggtt cgggatggtc gcgggacctg tgctcggtgg gctgatgggc     540
ggtttctccc cccacgctcc gttcttcgcc gcggcagcct tgaacggcct caatttcctg     600
acgggctgtt tccttttgcc ggagtcgcac aaaggcgaac gccggccgtt acgcggggag     660
gctctcaacc cgctcgcttc gttccggtgg gcccggggca tgaccgtcgt cgccgccctg     720
atggcggtct tcttcatcat gcaacttgtc ggacaggtgc cggccgcgct ttgggtcatt     780
ttcggcgagg atcgctttca ctgggacgcg accacgatcg gcatttcgct tgccgcattt     840
ggcattctgc attcactcgc ccaggcaatg atcaccggcc tgtagccgc ccggctcggc     900
gaaaggcggg cactcatgct cggaatgatt gccgacggca caggctacat cctgcttgcc     960
ttcgcgacac ggggatggat ggcgttcccg atcatggtcc tgcttgcttc gggtggcatc    1020
ggaatgccgg cgctgcaagc aatgttgtcc aggcaggtgg atgaggaacg tcaggggcag    1080
ctgcaaggct cactggcggc gctcaccagc ctgacctcga tcgtcggacc cctcctcttc    1140
acggcgatct atgcggcttc tataacaacg tggaacgggt gggcatggat tgcaggcgct    1200
gccctctact tgctctgcct gccggcgctg cgtcgcgggc tttggagcgg cgcagggcaa    1260
cgagccgatc gctga                                                     1275
```

<210> SEQ ID NO 26

<400> SEQUENCE: 26

000

<210> SEQ ID NO 27

<400> SEQUENCE: 27

000

<210> SEQ ID NO 28
<211> LENGTH: 40
<212> TYPE: DNA
<213> ORGANISM: Artificial sequence
<220> FEATURE:
<223> OTHER INFORMATION: Synthetic primer

<400> SEQUENCE: 28

```
gcaagttgaa aaattcacga aagttacacg ttactaaagg                            40
```

<210> SEQ ID NO 29
<211> LENGTH: 40
<212> TYPE: DNA
<213> ORGANISM: Artificial sequence
<220> FEATURE:
<223> OTHER INFORMATION: Synthetic primer

<400> SEQUENCE: 29
cactatcaac acactcttaa gcttgccttg ctcgtcggtg                40

<210> SEQ ID NO 30

<400> SEQUENCE: 30

000

<210> SEQ ID NO 31
<211> LENGTH: 40
<212> TYPE: DNA
<213> ORGANISM: Artificial sequence
<220> FEATURE:
<223> OTHER INFORMATION: Synthetic primer

<400> SEQUENCE: 31
gcttttgtaa atttgcataa aaataagaag cctgcatttg                40

<210> SEQ ID NO 32
<211> LENGTH: 39
<212> TYPE: DNA
<213> ORGANISM: Artificial sequence
<220> FEATURE:
<223> OTHER INFORMATION: Synthetic primer

<400> SEQUENCE: 32
tttagtaacg tgtaactttc gtgaatttttt caacttgcc                39

<210> SEQ ID NO 33

<400> SEQUENCE: 33

000

<210> SEQ ID NO 34
<211> LENGTH: 40
<212> TYPE: DNA
<213> ORGANISM: Artificial sequence
<220> FEATURE:
<223> OTHER INFORMATION: Synthetic primer

<400> SEQUENCE: 34
caccgacgag caaggcaagc ttaagagtgt gttgatagtg                40

<210> SEQ ID NO 35
<211> LENGTH: 40
<212> TYPE: DNA
<213> ORGANISM: Artificial sequence
<220> FEATURE:
<223> OTHER INFORMATION: Synthetic primer

<400> SEQUENCE: 35
gcttcttatt tttatgcaaa tttacaaaag cgactcatag                40

<210> SEQ ID NO 36

<400> SEQUENCE: 36

000

<210> SEQ ID NO 37
<211> LENGTH: 18

```
<212> TYPE: DNA
<213> ORGANISM: Artificial sequence
<220> FEATURE:
<223> OTHER INFORMATION: Synthetic primer

<400> SEQUENCE: 37
cttgccttgc tcgtcggt                                                 18

<210> SEQ ID NO 38
<211> LENGTH: 27
<212> TYPE: DNA
<213> ORGANISM: Artificial sequence
<220> FEATURE:
<223> OTHER INFORMATION: Synthetic primer

<400> SEQUENCE: 38
aagtgatagt caaaaggcat aacagtg                                       27

<210> SEQ ID NO 39

<400> SEQUENCE: 39

000

<210> SEQ ID NO 40
<211> LENGTH: 39
<212> TYPE: DNA
<213> ORGANISM: Artificial sequence
<220> FEATURE:
<223> OTHER INFORMATION: Synthetic primer

<400> SEQUENCE: 40
gacgagcaag gcaagcaatt atagtgaaag atgtgaagg                          39

<210> SEQ ID NO 41
<211> LENGTH: 41
<212> TYPE: DNA
<213> ORGANISM: Artificial sequence
<220> FEATURE:
<223> OTHER INFORMATION: Synthetic primer

<400> SEQUENCE: 41
accttttcca taattatctc tccttttta taatagtatg g                        41

<210> SEQ ID NO 42

<400> SEQUENCE: 42

000

<210> SEQ ID NO 43
<211> LENGTH: 33
<212> TYPE: DNA
<213> ORGANISM: Artificial sequence
<220> FEATURE:
<223> OTHER INFORMATION: Synthetic primer

<400> SEQUENCE: 43
agagataatt atgaaaaagg ttgcattagt tac                                33

<210> SEQ ID NO 44
<211> LENGTH: 33
<212> TYPE: DNA
<213> ORGANISM: Artificial sequence
<220> FEATURE:
<223> OTHER INFORMATION: Synthetic primer
```

<400> SEQUENCE: 44
ccttacaatt taattaaata ccataccacc gtc                                    33

<210> SEQ ID NO 45

<400> SEQUENCE: 45

000

<210> SEQ ID NO 46
<211> LENGTH: 32
<212> TYPE: DNA
<213> ORGANISM: Artificial sequence
<220> FEATURE:
<223> OTHER INFORMATION: Synthetic primer

<400> SEQUENCE: 46
gtatttaatt aaattgtaag gatcctagtc ag                                     32

<210> SEQ ID NO 47
<211> LENGTH: 35
<212> TYPE: DNA
<213> ORGANISM: Artificial sequence
<220> FEATURE:
<223> OTHER INFORMATION: Synthetic primer

<400> SEQUENCE: 47
gtacttttta tgagctctta actatttatc aattc                                  35

<210> SEQ ID NO 48

<400> SEQUENCE: 48

000

<210> SEQ ID NO 49
<211> LENGTH: 40
<212> TYPE: DNA
<213> ORGANISM: Artificial sequence
<220> FEATURE:
<223> OTHER INFORMATION: Synthetic primer

<400> SEQUENCE: 49
agagctcata aaaagtactc atagaattga ttaaaaaatg                             40

<210> SEQ ID NO 50
<211> LENGTH: 44
<212> TYPE: DNA
<213> ORGANISM: Artificial sequence
<220> FEATURE:
<223> OTHER INFORMATION: Synthetic primer

<400> SEQUENCE: 50 atgcctttg actatcactt atacatctcc tttaaatcca tttg            44

<210> SEQ ID NO 51
<211> LENGTH: 19
<212> TYPE: DNA
<213> ORGANISM: Artificial sequence
<220> FEATURE:
<223> OTHER INFORMATION: Synthetic primer

<400> SEQUENCE: 51
ctggaaaaga actcttagc            19

<210> SEQ ID NO 52
<211> LENGTH: 18
<212> TYPE: DNA
<213> ORGANISM: Artificial sequence
<220> FEATURE:
<223> OTHER INFORMATION: Synthetic primer

<400> SEQUENCE: 52
tgcggtggaa tacaatgg            18

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

        *******.**.:*:.::*:*.  *.*:*:*

RECOMBINANT MICROORGANISMS AND METHODS OF USE THEREOF

CROSS REFERENCE TO A RELATED APPLICATION

This application claims priority from Provisional Application No. 61/877,272 filed Sep. 12, 2013, the contents of which are hereby incorporated by reference.

SEQUENCE LISTING

Incorporated by reference in its entirety herein is a computer-readable nucleotide/amino acid sequence listing submitted concurrently herewith and identified as follows: 55,328 byte ASCII (text) file named "LT90US1-2014-09-24.txt" created on Sep. 24, 2014.

FIELD

The present invention relates to selection markers of use in the preparation of recombinant *Clostridium* spp.

BACKGROUND

Processes for producing recombinant organisms are known. They typically involve transformation of an organism with an exogenous nucleic acid vector, which may integrate with the host genome or remain in a stable independent (for example, extra-chromosomal) state.

Integration of an exogenous nucleic acid into the host genome involves a double-crossover event between the vector and an endogenous nucleic acid. Double-crossover recombination happens at frequencies which are too low to reliably identify integrants by chance alone. Therefore, a means to select for one or both crossovers has a huge benefit on the frequency of identification in both time and labour.

Selection markers of use in screening for recombination events are known. Such markers are typically protein coding sequences that confer a selective advantage (positive-selection) or disadvantage (counter-selection) to a host organism. A number of positive-selection and counter-selection markers are known and can be of use in screening for organisms in which a desired recombination event has occurred. A positive-selection marker typically comprises a gene that when expressed allows an organism to survive in a particular growth environment. A counter-selection marker typically comprises a gene that when expressed produces a toxin which is lethal to an organism.

In bacteria other than Clostridia, there is a plethora of counter-selection markers available but unfortunately either due to physiological or genetic reasons, the vast majority do not work in Clostridia.

It is an object of the invention to overcome one or more of the disadvantages of the prior art, or to at least to provide the public with a useful choice.

SUMMARY OF INVENTION

In a first aspect, the invention provides the use of ThiK and/or PheS as a counter-selection marker in a method for producing a recombinant microorganism from a parental microorganism, wherein the parental microorganism is a *Clostridium* spp., and wherein the PheS includes at least one alteration compared to a wild-type PheS such that in use phenylalanine tRNA synthetase is able to aminoacylate tRNA using a phenylalanine analogue.

In a second aspect, the invention provides the use of a nucleic acid encoding ThiK and/or PheS in a plasmid of use in producing a recombinant microorganism from a parental microorganism, wherein the parental microorganism is a *Clostridium* spp., and wherein the PheS includes at least one alteration compared to a wild-type PheS such that in use phenylalanine tRNA synthetase is able to aminoacylate tRNA using a phenylalanine analogue.

In a third aspect, the invention provides the use of a plasmid comprising a nucleic acid encoding ThiK and/or PheS for producing a recombinant microorganism from a parental microorganism, wherein the parental microorganism is a *Clostridium* spp., and wherein the PheS includes at least one alteration compared to a wild-type PheS such that in use phenylalanine tRNA synthetase is able to aminoacylate tRNA using a phenylalanine analogue.

In a fourth aspect, the invention provides a method for the production of a recombinant microorganism from a parental microorganism, the method comprising at least the steps of:

a) transformation of a parental microorganism with a plasmid comprising
  1. at least one nucleic acid sequence encoding at least one counter selection marker chosen from the group consisting of PheS and ThiK, wherein the PheS includes at least one alteration compared to a wild-type PheS such that in use phenylalanine tRNA synthetase is able to aminoacylate tRNA using a phenylalanine analogue;
  2. at least one nucleic acid sequence encoding at least one positive selection marker; and,
  3. two nucleic acid sequences homologous to selected regions around a target location within the genome of the parental microorganism, which allow for the recombination of the plasmid with the genome of the parental microorganism;
b) selecting one or more microorganisms that express the at least one positive selection marker; and,
c) selecting one or more microorganisms which do not express the at least one counter selection marker.

In one embodiment, the selection steps b) and c) are conducted simultaneously. In another embodiment, the selection steps b) anc c) are conducted sequentially.

In one embodiment, the plasmid further comprises at least one nucleic acid sequence of interest to be inserted into the parental genome.

In a fourth aspect, the invention provides a nucleic acid encoding a PheS, wherein the PheS is altered compared to a wild-type PheS such that in use phenylalanine tRNA synthetase is able to aminoacylate tRNA using a phenylalanine analogue, and wherein the wild-type PheS is derived from a *Clostridium* spp or is a functionally equivalent variant thereof.

In a fifth aspect, the invention provides a nucleic acid vector comprising a nucleic acid according to the fourth aspect of the invention. In one embodiment, the vector is a plasmid.

In one embodiment, the vector is a plasmid and also comprises one or more of:

a. at least one nucleic acid sequence encoding at least one positive selection marker; and,
b. two nucleic acid sequences homologous to selected regions around a target location within the genome of a parental microorganism, which allow for the recombination of the plasmid with the genome of the parental microorganism.

In one embodiment, the plasmid further comprises at least one nucleic acid sequence of interest which is desired to be inserted into the genome of a parental microorganism.

In a sixth aspect, the invention provides a PheS, wherein the PheS comprises one or more alteration compared to a wild-type PheS such that in use phenylalanine tRNA synthetase is able to aminoacylate tRNA using a phenylalanine analogue, and wherein the wild-type PheS is derived from a *Clostridium* spp or is a functionally equivalent variation thereof.

In a seventh aspect, the invention provides a cell comprising a nucleic acid according to the fourth aspect of the invention, a vector according to the fifth aspect of the invention and/or a PheS according to the sixth aspect of the invention.

In one embodiment of the above aspects of the invention, the wild-type PheS and/or wild-type nucleic acid encoding PheS is derived from a *Clostridium* spp or is a functionally equivalent variant thereof.

In one embodiment of the above aspects and embodiment of the invention, the at least one alteration in PheS compared to a wild-type includes one or more amino acid substitution, deletion and/or addition.

In one particular embodiment of the above aspects and embodiments of the invention, the at least one alteration in PheS is located within the substrate specificity site. In one embodiment, the substrate specificity site is located between amino acids 306 and 313 read relative to the amino acid position of wild-type PheS of *C. autoethanogenum* (SEQ ID 21). In one embodiment, the at least one alteration is an amino acid substitution at position 311. In one embodiment, the at least one alteration is substitution of Ala for Gly at amino acid 311.

In one embodiment of the above aspects and embodiments of the invention, the PheS is derived from *Clostridium autoethanogenum* or is a functionally equivalent variant thereof.

In one embodiment of the above aspects and embodiments of the invention, the alterned PheS comprises the amino acid sequence of SEQ ID No. 21.

In one embodiment of the above aspects and embodiments of the invention, the nucleic acid encoding PheS which includes at least one alteration compared to a wild-type PheS, comprises at least one alteration compared to a nucleic acid encoding a wild-type PheS. In one embodiment, the at least one alteration in a nucleic acid encoding PheS includes one or more nucleotide substitution, deletion and/or addition. In one embodiment, the one or more alteration in the nucleic acid sequence is located within a region of the nucleic acid which encodes the substrate specificity site of PheS. In one embodiment, the region of a nucleic acid encoding the substrate specificity site is located between bases 918 and 939, read relative to the nucleotide position of the gene encoding wild-type PheS of *C. autoethanogenum* (SEQ ID 12). In one embodiment, the at least one alteration is a nucleotide substitution at base 932. In one embodiment, the at least one alteration is substitution of C for G at base 932.

In one embodiment of the above aspects and embodiments of the invention, the nucleic acid encoding PheS is derived from *Clostridium autoethanogenum* or is a functionally equivalent variant thereof.

In one embodiment of the above aspects and embodiments of the invention, the nucleic acid encoding altered PheS comprises the sequence of SEQ ID No. 14.

In one embodiment of the above aspects and embodiments of the invention, the phenylalanine analogue is chosen from chlorophenylalanine, fluorophenylalanine and bromophenylalanine. In one particular embodiment, the phenylalanine analogue is chosen from DL-4-chlorophenylalanine and p-chlorophenylalanine, p-fluoro-L-phenylalanine, p-fluoro-DL-phenylalanine, p-bromo-L-phenylalanine.

In one embodiment of the above aspects and embodiments of the invention, the ThiK and/or the nucleic acid encoding ThiK is from Herpes Simplex Virus 1 or Herpes Simplex Virus 2 (HSV-TK), VZV, CMV, HHV7, HHV7, HHV8, EBV or is a functionally equivalent variant of any one or more thereof.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which:

FIG. 3: Shows pairwise translated nucleotide sequence alignment of pheS from *E. coli* MG1655 (Seq ID 13) and *C. autoethanogenum* with putative substrate specificity region bold and underlined.

FIG. 9A: 433s and 388a (faint band), FIG. 9B: 211s, and 287a. FIG. 9C: 287a, and 433

BRIEF DESCRIPTION OF SEQUENCE INFORMATION

Figure 1:
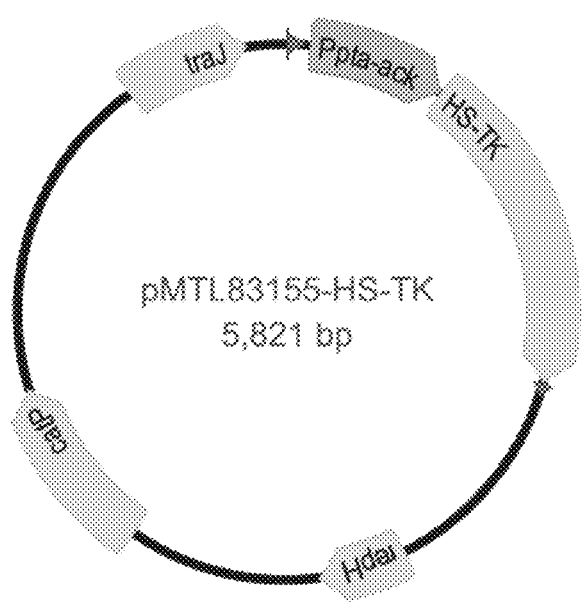
FIG. 1: Shows the map of plamid pMTL83155-HSV-tk

Prior to the figures shown herein after, the specification includes details of the sequences of nucleic acids and polypeptides relevant to the invention. The following sequences are provided:

Seq. ID.1: Nucleic acid sequence of pMK-RQ-Hsv-tk
Seq. ID.2: Nucleic acid sequence of pMTL83155-Hsv-tk
Seq. ID.3: Nucleic acid sequence of pMTL83155
Seq. ID.4: Nucleic acid sequence of primer repHf
Seq. ID.5: Nucleic acid sequence of primer catr
Seq. ID.6: Nucleic acid sequence of primer fD1
Seq. ID.7: Nucleic acid sequence of primer rP2
Seq. ID.8: 16s rRNA nucleic acid sequence of LZ-pMTL83155-1 obtained using primer rP2
Seq. ID.9: 16s rRNA nucleic acid sequence of LZ-pMTL83155-2 obtained using primer rP2
Seq. ID.10: 16s rRNA nucleic acid sequence of LZ-pMTL83155-hsv-tk-1 obtained using primer rP2
Seq. ID.11: 16s rRNA nucleic acid sequence of LZ-pMTL83155-hsv-tk-2 obtained using primer rP2
Seq. ID.12: Nucleic acid sequence encoding pheS of *C. autoethanogenum*
Seq. ID.13: Nucleic acid sequence encoding pheS of *E. coli* MG1655
Seq. ID.14: Nucleic acid sequence encoding altered pheS* of *C. autoethanogenum*
Seq. ID.15: Forward primer sequence used for confirming the presence of PheS plasmid—M13F
Seq. ID.16: Reverse primer sequence used for confirming the presence of PheS plasmid—M13R
Seq. ID.17: Synthetic promoter PpheS*
Seq. ID.18: Nucleotide sequence of pMTL85151 pheS*
Seq. ID. 19: Nucleic acid sequence encoding HSV-TK of Human Herpesvirus 1 (Herpes simplex virus type 1)
Seq. ID. 20: Amino acid sequence of PheS of *E. coli* MG1655
Seq. ID. 21: Amino acid sequence of PheS of *C. autoethanogenum*
Seq. ID. 22: Nucleic acid sequence encoding ThiK of Human Herpesvirus 1 (Herpes simplex virus type 1)
Seq. ID. 23: Nucleic acid sequence encoding CatP of *Clostridium perfringens*
Seq. ID. 24: Nucleic acid sequence encoding ErmB of *Peptoclostridium difficile*
Seq. ID. 25: Nucleic acid sequence encoding TetA of *Escherichia coli*
Other sequences of relevance to the invention are described elsewhere herein. For example, see Table 3 in Example 2.

DETAILED DESCRIPTION OF THE INVENTION

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The production of recombinant microorganisms can involve introducing an exogenous nucleic acid into a parental microorganism, with a double-crossover recombination event occurring between the exogenous nucleic acid and the genome of the microorganism so that at least one desired genetic alteration can be introduced into the genome. Double-crossover recombination happens at frequencies that are typically too low to reliably identify integrants by chance alone. Therefore, the inventors believe that a means to select for one or both crossovers has a huge benefit on the frequency of identification in both time and labour. It has been noted by the inventors in their lab that the frequency of single-crossover recombination although low, can be found by screening an appropriate number of colonies, however, this has not been seen to be the case with the second crossover event. The present invention provides a means to select for the second event by counter selecting against a condition lethal gene product present in the exogenous nucleic acid introduced into the parental microorganism. This means that in any microorganisms in which only a single-crossover event has occurred in the presence of a counter selecting agent the expression of the condition legal gene product, will kill any cell which has not undergone the secondary crossover event and released the nucleic acid containing the gene encoding the counter selection marker.

Counter-selection markers are known. However, they are not necessarily transferable for use in different genera of bacteria. Unfortunately either due to physiological or genetic reasons, the vast majority do not work in Clostridia. The inventors have surprisingly identified that ThiK and an altered version of PheS can be used as counter-selection markers in *Clostridium* spp.

Definitions

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of organisms which differ from the organism to which they are to be introduced, or they may be artificially or recombinantly created.

A "genetic modification" should be taken broadly and is intended to include, for example, introducing a mutation to a genetic site, adding to or removing from the genome one or more nucleotides, substitution of one or more nucleotides with different nucleotides, substitution of a gene, removal of a gene, addition of a gene and the like.

Reference may be made herein to an "altered PheS", a "PheS which is altered" or a PheS including one or more or at least one "alteration" compared to a wild-type PheS such that in use phenylalanine tRNA synthetase is able to aminoacylate tRNA using a phenylalanine analogue. An "alteration" should be considered broadly and includes, for example, one or a combination of substitution of one or more amino acid, deletion of one or more amino acid, and/or addition of one or more amino acid compared to a wild-type PheS. An "altered" PheS may also include one or more alterations in addition to those that allow phenylalanine tRNA synthetase to aminoacylate tRNA using a phenylalanine analogue, provided it is still able to substantially perform its desired function.

Reference may be made herein to a nucleic acid encoding a PheS comprising one or more alterations compared to a nucleic acid which encodings a wild-type PheS. An "alteration" should be considered broadly and includes, for example, one or a combination of substitution of one or more nucleotides, deletion of one or more nucleotide, and/or addition of one or more nucleotide compared to a nucleic acid encoding a wild-type PheS. The nucleic acid may also include one or more alterations in addition to those that allow phenylalanine tRNA synthetase to aminoacylate tRNA using a phenylalanine analogue, provided the PheS is still able to substantially perform its desired function.

One or more alteration of PheS or a nucleic acid encoding PheS may be described herein with reference to a specific region or amino acid or nucleotide position in a wild-type PheS (or nucleic acid encoding same) from a specific organism. It will be appreciated that the precise location of a particular region, amino acid or nucleotide may vary slightly from one PheS or nucleic acid encoding PheS to another, for example in different strains or species of organisms. To account for this variation, where the location of a specific region, nucleotide or amino acid is referred to herein, it is described as being "read in relation to" or "read relative to" the amino acid position of wild-type PheS of *C. autoethanogenum* (SEQ ID No. 21) (or to the wild-type Phe-S from *C. ljungdahlii* DSM13528 (GenBank: ADK16487.1)) or the nucleotide position of the nucleic acid encoding PheS of *C. autoethanogenum* (SEQ ID 12 herein) (or to the wild-type Phe-S from *C. ljungdahlii* DSM13528 (GenBank: ADK16487.1), wherein the first position amino acid in SEQ ID 21 (or ADK16487.1) and the first nucleotide in SEQ ID 12 (or ADK16487.1) are position 1. Such phrases should be taken broadly and are intended to encompass equivalent regions, amino acids or nucleotides in other PheS proteins (or nucleic acids encoding same) even though they may be at a different location. Persons of skill in the art to which the invention relates will be able to readily identify the location or position of a particular region, amino acid or nucleotide in a particular PheS or nucleic acid encoding same through routine sequence alignment and with the information contained herein.

Reference to a particular region of a PheS or nucleic acid "between" two particular amino acids or nucleotides should be taken to mean a region comprising said nucleotides or amino acids. In other words, the region includes the terminal nucleotides or amino acids referred to. For example, a substrate specific site between amino acids at position 306 and 313 includes the amino acids present at positions 306 and 313.

The term "phenylalanine analogue" should be taken broadly and includes an analogue or derivative of phenylalanine that can be incorporated into peptides and proteins in the place of phenylalanine resulting in toxicity to a microorganism. In one embodiment, the phenylalanine analogue is chosen from chlorophenylalanine, fluorophenylalanine and bromophenylalanine. In one particular embodiment, the phenylalanine analogue is chosen from DL-4-chlorophenylalanine and p-chlorophenylalanine, p-fluoro-L-phenylalanine, p-fluoro-DL-phenylalanine, p-bromo-L-phenylalanine. Skilled persons may readily appreciate other phenylalanine analogues of use in the invention.

Reference may be made herein to a nucleic acid vector including a "nucleic acid sequence of interest" or like phrases. Such phrases should be taken broadly and include one or more nucleotide, gene, promoter, regulatory sequence, other genetic element and may be coding or non-coding. It may include a nucleotide sequence which is designed to introduce one or more genetic modification to one or more target location in the host genome, including one or a combination of a deletion, addition or subsitituion of one or more nucleotides. In some embodiments, the nucleic acid or nucleic acid sequence of interest may be designed to delete a gene present in the genome of the parental microorganism.

The expressions "target location" and "target nucleic acid sequence" as used herein should be taken broadly to include any site, region or nucleotide sequence in a parental or host genome where it is desired to introduce one or more genetic modification (including insertion, deletion and/or substitution of one or more nucleotides), and includes a gene, intergenic region, promoter and/or regulatory sequence of interest, for example.

Reference may be made herein to a vector of the invention including "two nucleic acid sequences homologous to selected regions around a target location" within the genome of a parental microorganism. Such nucleic acid sequences may also be referred to herein as "homology arms".

Reference may be made herein to proteins (PheS and/or ThiK) or nucleic acids encoding such proteins being "from" or "derived from" a particular organism. This should be taken broadly to mean that the protein or nucleic acid has the sequence of the relevant protein or nucleic acid encoding the relevant protein in that organism. It should not be taken to mean that the protein or nucleic acid has been physically taken from that organism. Such proteins and nucleic acids may be made using chemical synthesis and the like, for example.

A "parental microorganism" is a microorganism used to generate a recombinant microorganism according to the invention. In one embodiment, the parental microorganism may be one that occurs in nature (ie a wild type microorganism) or one which has been previously modified (a genetically modified or recombinant microorganism). According to the present invention, a "parental microorganism" is a *Clostridium* spp.

Skilled persons will be able to readily identify *Clostridium* ssp. microorganisms of use in the invention. However, by way of example, the group may include: *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Clostridium coskatii, Clostridium acetobutylicum, Clostridium beijerinckii, Clostridium sacharoperbutylacetonicum, Clostridium saccharobutylicum, Clostridium thermocellum, Clostridium cellulolyticum, Clostridium phytofermentans, Clostridium pasterianum, Clostridium kluyveri, Clostridium difficile, Clostridium botulinum, Clostridium sporogenes, Clostridium perfringens, Clostridium acetobutylicum, Clostridium acidisoli, Clostridium aciditolerans, Clostridium acidurici, Clostridium aerotolerans, Clostridium akagii, Clostridium aldenense, Clostridium algidicarnis, Clostridium algidixylanolyticum, Clostridium alkalicellulosi, Clostridium aminovalericum, Clostridium amygdalinum, Clostridium arcticum, Clostridium argentinense, Clostridium aurantibutyricum, Clostridium baratii, Clostridium botulinum, Clostridium bowmanii, Clostridium butyricum, Clostridium beijerinckii, Clostridium cadaveris, Clostridium caminithermale, Clostridium carboxidivorans, Clostridium carnis, Clostridium celatum, Clostridium celerecrescens, Clostridium cellulolyticum, Clostridium cellulosi, Clostridium chartatabidum, Clostridium clostridioforme, Clostridium coccoides, Clostridium cochlearium, Clostridium cocleatum, Clostridium colinum, Peptoclostridium difficile, Clostridium diolis, Clostridium disporicum, Clostridium drakei, Clostridium durum, Clostridium esterteticum, Clostridium fallax, Clostridium felsineum, Clostridium ervidum, Clostridium fimetarium, Clostridium formicaceticum, Clostridium ghonii, Clostridium glycolicum, Clostridium glycyrrhizinilyticum, Clostridium haemolyticum, Clostridium halophilum, Clostridium tetani, Clostridium perfringens, Clostridium phytofermentans, Clostridium piliforme, Clostridium polysaccharolyticum, Clostridium populeti, Clostridium propionicum, Clostridium proteoclasticum, Clostridium proteolyticum, Clostridium psychrophilum, Clostridium puniceum, Clostridium puri, Clostridium putrefaciens, Clostridium putrificum, Clostridium quercicolum, Clostridium quinii, Clostridium ramosum, Clostridium roseum, Clostridium saccharobutylicum, Clostridium saccharolyticum, Clostridium saccharoperbutylacetonicum, Clostridium sardiniense, Clostridium* stercorarium, *Clostridium sticklandii*, *Clostridium paradoxum*, *Clostridium paraperfringens*, *Clostridium paraputrificum*, *Clostridium pascui*, *Clostridium pasteurianum*, *Clostridium novyi*, *Clostridium septicum*, *Clostridium histolyticum*, *Clostridium hydroxybenzoicum*, *Clostridium hylemonae*, *Clostridium innocuum*, *Clostridium kluyveri*, *Clostridium lactatifermentans*, *Clostridium lacusfryxellense*, *Clostridium laramiense*, *Clostridium lentocellum*, *Clostridium lentoputrescens*, *Clostridium methoxybenzovorans*, *Clostridium methylpentosum*, *Clostridium nitrophenolicum*, *Clostridium novyi*, *Clostridium oceanicum*, *Clostridium oroticum*, *Clostridium oxalicum*, *Clostridium tertium*, *Clostridium tetani*, *Clostridium tetanomorphum*, *Clostridium thermaceticum*, *Clostridium thermautotrophicum*, *Clostridium thermoalcaliphilum*, *Clostridium thermobutyricum*, *Clostridium thermocellum*, *Clostridium thermocopriae*, *Clostridium thermohydrosulfuricum*, *Clostridium thermolacticum*, *Clostridium thermopalmarium*, *Clostridium thermopapyrolyticum*, *Clostridium thermosaccharolyticum*, *Clostridium thermosulfiirigenes*, *Clostridium tyrobutyricum*, *Clostridium uliginosum*, *Clostridium ultunense*, *Clostridium villosum*, *Clostridium viride*, *Clostridium xylanolyticum*, *Clostridium xylanovorans*, *Clostridium bifermentans*, and *Clostridium sporogenes*.

In one particular embodiment the parental organism is selected from a group of acetogenic *Clostridium* spp. In one particular embodiment, the parental microorganism is selected from the group of acetogenic carboxydotrophic organisms comprising the species *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, and *Clostridium coskatii*.

In a one embodiment, the parental microorganism is selected from a cluster of carboxydotrophic Clostridia comprising the species *C. autoethanogenum*, *C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* P11$^T$" (ATCC BAA-622) (WO 2008/028055), and related isolates such as "*C. coskatii*" (US patent 2011/0229947), and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a GC composition of around 32% mol (Abrini et al., 1994; Köpke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde: ferredoxin oxidoreductase (Köpke et al., 2010, 2011). The organization and number of Wood-Ljungdahl pathway genes, responsible for gas uptake, has been found to be the same in all species, despite differences in nucleic and amino acid sequences (Köpke et al., 2011).

The strains of the cluster all have a similar morphology and size (logarithmic growing cells are between 0.5-0.7×3-5 µm) are mesophilic (optimal growth temperature between 30-37° C.) and strictly anaerobe (Abrini et al., 1994; Tanner et al., 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Köpke et al., 2011; Tanner et al., 1993)(WO 2008/028055). Indole production has been observed with all species. However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotrophic to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. The invention can be anticipated to work across not only these strains, but across all Clostridia species, although there may be differences in performance.

In particular embodiments, the parental microorganism is selected from the group comprising *Clostridium autoethanogenum*, *Clostridium ljungdahlii*, and *Clostridium ragsdalei*. In one embodiment, the group also comprises *Clostridium coskatii*. In one particular embodiment, the parental microorganism is *Clostridium autoethanogenum* DSM23693.

A parental microorganism may or may not contain nucleic acids encoding phenylalanine tRNA synthetase or express phenylalanine tRNA synthetase.

Throughout this specification exemplary sequence information is provided for PheS, altered PheS and ThiK proteins/peptides and nucleic acids encoding same. This information is provided to identify exemplary proteins/peptides and nucleic acids applicable to the invention and to allow a skilled person to practise specific embodiments of the invention without undue experimentation. It should be appreciated that nucleic acid and amino acid sequences may differ from one microorganism to another. Accordingly, the invention should not be construed as being limited to these specific embodiments but rather to extend to proteins/peptides and nucleic acids having different sequences but which are substantially capable of performing the same function. For PheS the desired function (as a subunit of phenylalanine tRNA synthetase) is aminoacylation of tRNA$^{Phe}$ with phenylalanine. For altered PheS the desired function (as a subunit of phenylalanine tRNA synthetase) is aminoacylation of tRNA with a phenylalanine analogue. For ThiK the desired function is to catalyse the reaction:

Thd+ATP→TMP+ADP where Thd is deoxythymidine, ATP is adenosine 5'-triphosphate, TMP is deoxythymidine 5'-phosphate and ADP is adenosine 5'-diphosphate.

Typically, such alternative or variant proteins/peptides will have at least approximately 75% amino acid sequence similarity to a PheS (including an altered PheS) or ThiK protein exemplified herein. In particular embodiments, such alternative proteins will have at least approximately 80%, 85%, 90%, 95% or 99% sequence similarity to a PheS (including an altered PheS) or ThiK exemplified herein. In particular embodiments, such alternative proteins will have at least approximately 75%, 80%, 85%, 90%, 95% or 99% sequence identity to a PheS (including an altered PheS) or ThiK exemplified herein. At the nucleic acid level, genes encoding such alternative or variant proteins will typically have at least approximately 75% sequence homology to a nucleic acid encoding a PheS (including an altered PheS) or ThiK exemplified herein. In particular embodiments, such variant or alternative nucleic acids will have at least approximately 80%, 85%, 90%, 95% or 99% sequence homology to a nucleic acid encoding a PheS (including an altered PheS) or ThiK exemplified herein. In one particular embodiment, such nucleic acids will have at least approximately 75%, 80%, 85%, 90%, 95% or 99% sequence identity to a nucleic acid encoding a PheS (including an altered PheS) or ThiK exemplified herein. Alternative or variant nucleic acids or proteins/peptides as described may be referred to herein as "functionally equivalent variants".

It should also be appreciated that the functionally equivalent variant of PheS, altered PheS, or ThiK need not have the same level of activity as a protein/peptide of which it is a variant. All that is required is that some level of the desired activity is retained. Assays of use in assessing the activity of PheS, an altered PheS or ThiK will be known by skilled persons. However, by way of example: The function or activity of Phe S can be tested using methods which measure aminoacylation. The authors used velocities of aminoacylation and kinetic parameters of pheS to test activity variations of pheS in utilising phenylalanine (Kast et al., 1991 (J. Mol. Biol. 222: 99-124)). The function or activity of an altered PheS can be conducted by observing growth in the presence of a toxic analogue of phenylanine using methods known for culturing or growing microorganisms (Kast et al., 1991 (J. Mol. Biol. 222: 99-124)). The function or activity of ThiK can be tested using an activity assay as described by Brockenbrough et al (Nucl Med. Biol. 2007, 34(6):619-23) and Jonsson & McIvor (Anal Biochem. 1991, 199(2):232-7) or with commercially available ELISA kits as for example from BioVendor (Cat. No. 901/902).

Reference to "transforming" a parental microorganism should be taken broadly to include any means of transferring or introducing an exogenous nucleic acid into a microorganism which are known in the art. By way of example, "transforming" includes, but is not limited to transfection, transduction, conjugation, and electroporation.

Aspects and Embodiments of Invention

The invention provides the use of ThiK and/or PheS as a counter-selection marker in a method for producing a recombinant microorganism from a parental microorganism. It also provides nucleic acid(s) encoding ThiK and/or PheS, nucleic acid vectors comprising said nucleic acid(s), and the use of said nucleic acid(s) and/or plasmids for producing a recombinant microorganism from a parental microorganism. In addition, the invention provides a method of producing a recombinant microorganism from a parental microorganism. In accordance with the invention, the parental microorganism is a *Clostridium* spp., as described herein before, and the PheS includes at least one alteration compared to a wild-type PheS such that in use phenylalanine tRNA synthetase is able to aminoacylate tRNA using a phenylalanine analogue.

PheS

PheS is the alpha subunit of the two subunit protein phenylalanine tRNA synthetase. Phenylalanine tRNA synthetase is responsible for aminoacylation of tRNA$^{Phe}$ with phenylalanine which is critical for protein production in a cell. The enzyme catalyses the acelation of phenylalanine to its cognate tRNA. The resultant tRNA$^{Phe}$ is delivered to the ribosome by elongation factors then subsequently bound to its cognate anti-codon present upon the mRNA. Once bound, the amino acid is covalently attached to its preceding amino-acid thereby increasing the peptide chain.

A PheS of the invention is one which includes at least one alteration compared to a wild type PheS such that in use phenylalanine tRNA synthetase is able to aminoacylate tRNA using phenylalanine analogues. Incorporation of phenylananie analogues into cellular proteins results in unstable or non-functional proteins. Thus, any cell including the altered PheS will typically not be able to survive.

The wild-type PheS on which the altered PheS is based may be from any appropriate source including any number of different self replicating organisms, such as plants, animals, fungi and microorganisms. In one particular embodiment, the PheS is from a microorganism. In one embodiment, the PheS is from a *Clostridium* spp or is a functionally equivalent variant thereof. By way of example only, the *Clostridium* spp. may include:

*Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Clostridium coskatii, Clostridium acetobutylicum, Clostridium beijerinckii, Clostridium sacharoperbutylacetonicum, Clostridium saccharobutylicum, Clostridium thermocellum, Clostridium cellulolyticum, Clostridium phytofermentans, Clostridium pasterianum, Clostridium kluyveri, Clostridium difficile, Clostridium botulinum, Clostridium sporogenes, Clostridium perfringens, Clostridium acetobutylicum, Clostridium acidisoli, Clostridium aciditolerans, Clostridium acidurici, Clostridium aerotolerans, Clostridium akagii, Clostridium aldenense, Clostridium algidicarnis, Clostridium algidixylanolyticum, Clostridium alkalicellulosi, Clostridium aminovalericum, Clostridium amygdalinum, Clostridium arcticum, Clostridium argentinense, Clostridium aurantibutyricum, Clostridium baratii, Clostridium botulinum, Clostridium bowmanii, Clostridium butyricum, Clostridium beijerinckii, Clostridium cadaveris, Clostridium caminithermale, Clostridium carboxidivorans, Clostridium carnis, Clostridium celatum, Clostridium celerecrescens, Clostridium cellulolyticum, Clostridium cellulosi, Clostridium chartatabidum, Clostridium clostridioforme, Clostridium coccoides, Clostridium cochlearium, Clostridium cocleatum, Clostridium colinum, Clostridium difficile, Clostridium diolis, Clostridium disporicum, Clostridium drakei, Clostridium durum, Clostridium esterteticum, Clostridium fallax, Clostridium felsineum, Clostridium ervidum, Clostridium fimetarium, Clostridium*

*formicaceticum, Clostridium ghonii, Clostridium glycolicum, Clostridium glycyrrhizinilyticum, Clostridium haemolyticum, Clostridium halophilum, Clostridium tetani, Clostridium perfringens, Clostridium phytofermentans, Clostridium piliforme, Clostridium polysaccharolyticum, Clostridium populeti, Clostridium propionicum, Clostridium proteoclasticum, Clostridium proteolyticum, Clostridium psychrophilum, Clostridium puniceum, Clostridium puri, Clostridium putrefaciens, Clostridium putrificum, Clostridium quercicolum, Clostridium quinii, Clostridium ramosum, Clostridium roseum, Clostridium saccharobutylicum, Clostridium saccharolyticum, Clostridium saccharoperbutylacetonicum, Clostridium sardiniense, Clostridium stercorarium, Clostridium sticklandii, Clostridium paradoxum, Clostridium paraperfringens, Clostridium paraputrificum, Clostridium pascui, Clostridium pasteurianum, Clostridium novyi, Clostridium septicum, Clostridium histolyticum, Clostridium hydroxybenzoicum, Clostridium hylemonae, Clostridium innocuum, Clostridium kluyveri, Clostridium lactatifermentans, Clostridium lacusfryxellense, Clostridium laramiense, Clostridium lentocellum, Clostridium lentoputrescens, Clostridium methoxybenzovorans, Clostridium methylpentosum, Clostridium nitrophenolicum, Clostridium novyi, Clostridium oceanicum, Clostridium oroticum, Clostridium oxalicum, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosulfurigenes, Clostridium tyrobutyricum, Clostridium uliginosum, Clostridium ultunense, Clostridium villosum, Clostridium viride, Clostridium xylanolyticum, Clostridium xylanovorans, Clostridium bifermentans,* and *Clostridium sporogenes.*

In certain embodiments, the PheS is from a microorganism selected from the group of *Clostridium* spp or is a functionally equivalent variant thereof. In one embodiment, the PheS is from a microorganism selected from a group of acetogenic *Clostridium* spp or is a functionally equivalent variant thereof. In one particular embodiment, PheS is from a microorganisms selected from the group of acetogenic carboxydotrophic organisms comprising the species *Clostridium* autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, and *Clostridium* coskatii, or is a functionally equivalent variant of any one or more thereof.

In a one embodiment, PheS is selected from a cluster of carboxydotrophic Clostridia comprising the species *C. autoethanogenum, C. ljungdahlii,* and *"C. ragsdalei"* and related isolates, which have been described herein before.

By way of example only, appropriate wild-type PheS proteins (and corresponding nucleic acid sequences) include those described in public databases, such as GenBank, as follows: PheS from *Clostridium ljungdahlii* DSM13528 (GenBank ADK16487.1); *Clostridium carboxidivorans* P7 (GenBank: EET86555.1); phenylalanyl-tRNA synthetase subunit alpha [*Clostridium kluyveri*] WP_012620882.1; phenylalanyl-tRNA synthetase subunit alpha [*Clostridium perfringens* str. 13] GenBank: BAB81592.1; phenylalanyl-tRNA synthetase subunit alpha [*Clostridium botulinum* A str. ATCC 3502] GenBank: YP_001255621.1; phenylalanyl-tRNA synthetase subunit alpha [*Clostridium sporogenes*] GenBank: WP_003495653.1; phenylalanyl-tRNA synthetase subunit alpha [*Clostridium beijerinckii* NCIMB 8052] GenBank: YP_001308703.1; phenylalanyl-tRNA synthetase subunit alpha [*Clostridium acetobutylicum* ATCC 824] GenBank: NP_348973.1; phenylalanyl-tRNA synthetase subunit alpha [*Clostridium thermocellum* ATCC 27405] GenBank: YP_001036648.1. In one embodiment, the PheS is from *C. autoethanogenum* and has the amino acid sequence of SEQ ID No.21. Functionally equivalent variants of these exemplary proteins may also be of use.

In one embodiment, the at least one alteration in PheS compared to a wild-type PheS is located within a region which comprises the substrate specificity site. In one embodiment, the substrate specificity site is located between amino acids 306 and 313, read in relation to the wild-type PheS from *C. autoethanogenum* SEQ ID No. 21 (or to the wild-type Phe-S from *C. ljungdahlii* DSM13528 (GenBank: ADK16487.1)).

It should be appreciated that the precise location of the substrate specificity site may vary from one particular PheS protein to another. Accordingly, the invention should be taken to include PheS proteins which have been altered outside of the site defined by amino acids 306 to 313 above, and confer on phenylalanine tRNA synthetase the ability to aminoacylate tRNA using phenylalanine analogues. Persons of general skill in the art to which the invention relates will readily be able to identify the appropriate site based on alignment of the amino acid sequence with that of *C. autoethanogenum* SEQ ID 21 (or to the wild-type Phe-S from *C. ljungdahlii* DSM13528 (GenBank ADK16487.1), described above. However, by way of example, in PheS in *E. coli* the substrate specificity site is defined by amino acids at positions 289 to 296.

In one embodiment, the at least one alteration is one or more amino acid substitution, addition and/or deletion. In one embodiment, the at least one alteration is an amino acid substitution at position 311, read relative to the amino acid sequence of *Clostridium autoethanogenum* PheS (SEQ ID 21). In one embodiment, the at least one alteration is substitution of Ala for Gly at amino acid 311. In other embodiments, the alternation is one or a combination of amino acid substitutions at positions 310 and 312, read relative to the amino acid sequence of *Clostridium autoethanogenum* PheS (SEQ ID 21).

In one embodiment, the altered PheS comprises or consists of the amino acid sequence of altered pheS* of *C. autoethanogenum.*

The invention also relates to nucleic acids encoding an altered PheS of the invention. In one embodiment, the at least one alteration is located within a region of the nucleic acid which encodes the substrate specificity site, as referred to herein before.

In one embodiment, the region encoding the substrate specificity site is located between bases 918 and 939, read in relation to the nucleic acid encoding PheS in *C. autoethanogenum* (SEQ ID 12 herein) (or to the wild-type Phe-S from *C. ljungdahlii* DSM13528 (GenBank: ADK16487.1). However, the site may differ from one nucleic acid to another (for example nucleic acids from different species or organisms), to reflect the precise location of the substrate specificity site on a wild-type PheS protein, as described hereinbefore. Skilled persons will readily be able to identify the appropriate region in alternative nucleic acids through standard sequence alignments.

In one embodiment, the at least one alteration is one or more nucleotide substitution, addition and/or deletion.

In one embodiment, the at least one alteration is a nucleotide substitution at base 932 read relative to the *Clostridium autoethanogenum* gene encoding PheS (SEQ ID 12). In one embodiment, the at least one alteration is substitution of C for G at base 932. In one embodiment, the nucleic acid comprises or consists of the sequence of SEQ ID No. 14.

Nucleic acids encoding an altered PheS in accordance with the invention can be generated using any number of known methods in the art, based on the information herein, the amino acid sequence (and/or the nucleic acid sequence encoding the amino acid sequence) of exemplary wild-type PheS proteins, and the genetic code, for example. However, by way of example, they may be produced by chemical synthesis or via standard recombinant techniques.

By way of example, exemplary nucleic acids encoding wild-type PheS are provided herein and in publicly available databases such as GenBank as follows: *E. coli* K12 (NC_000913.2), Gene ID: 946223, EcoGene:EG10709; *Clostridium ljungdahlii* DSM 13528, GenBank: CP001666.1, GI:300433347.

It should be appreciated that a nucleic acid encoding an altered PheS can be codon optimised for the particular *Clostridium* spp. in which it is to be expressed. This can be achieved using standard codon optimisation techniques.

ThiK

ThiK is a protein which functions to catalyse the reaction:

Thd+ATP→TMP+ADP where Thd is deoxythymidine, ATP is adenosine 5'-triphosphate, TMP is deoxythymidine 5'-phosphate and ADP is adenosine 5'-diphosphate. HSV-TK, for example, catalyses the phosphorylation of deoxythymidine.

ThiK of use in the invention may be derived from any appropriate organism. However, by way of example, ThiK may be from Herpes Simplex Virus 1 or Herpes Simplex Virus 2 (HSV-TK), VZV, CMV, HHV7, HHV7, HHV8, EBV Alternatively, functionally equivalent variants of ThiK from HSV-TK could be used.

By way of example only, ThiK proteins include those described in public databases such as GenBank as follows: AB009254.2. Functionally equivalent variants of this exemplary protein may also be of use.

In one embodiment, the ThiK comprises the amino acid sequence of Human Herpesvirus 1 (Herpes simplex virus type 1).

The invention also relates to nucleic acids encoding a ThiK. Skilled persons will readily appreciate the appropriate nucleotide sequence of nucleic acids encoding ThiK, having regard to the amino acid sequence of the exemplary ThiK proteins provided herein, and the genetic code. However, by way of example, exemplary nucleic acids encoding ThiK are provided in public databases such as GenBank AB009254.2, JQ895546.1, AY575235.1, AF243479.1, AY575236.2, HQ123159.1

However, by way of example, the nucleic acids may have a nucleotide sequence of SEQ ID 19 or SEQ ID 22 as described herein.

In one embodiment, the nucleic acid encoding ThiK has the nucleotide sequence of SEQ ID No. 19.

Nucleic acids encoding a ThiK in accordance with the invention can be generated using any number of known methods in the art, based on the information herein, the amino acid sequence (and/or the sequence of nucleic acids encoding the amino acid sequence) of exemplary ThiK proteins, and the genetic code, for example. However, by way of example, they may be produced by chemical synthesis or via standard recombinant techinques.

It should be appreciated that a nucleic acid encoding ThiK can be codon optimised for the particular *Clostridium* spp in which it is to be expressed. This can be achieved using standard codon optimisation techniques.

Nucleic Acid Vectors

The invention also provides a nucleic acid vector comprising a nucleic acid which encodes ThiK and/or an altered PheS in accordance with the invention. The vector may be of any original or nature, as will be understood by persons skilled in the art to which the invention relates, including for example those suitable for cloning and expression and transformation.

In one embodiment, the nucleic acid vector is one suitable for generating a recombinant microorganism of the invention. In this embodiment, the nucleic acid vector is a plasmid which comprises at least a nucleic acid encoding an altered PheS and/or a ThiK as described herein before. In one particular embodiment, the vector further comprises at least:

(a) at least one nucleic acid sequence encoding at least one positive selection marker;
(b) two nucleic acid sequences homologous to selected regions around a target location or nucleic acid sequence within the genome of a parental microorganism, which allow for the recombination of the plasmid with the genome of the parental microorganism.

In one embodiment, the vector further comprises at least one nucleic acid of interest which is desired to be inserted or integrated into the genome of a parental microorganism.

In one embodiment, the nucleic acid encoding the positive selection marker is positioned on the plasmid vector outside of the homology arms. In another embodiment, the nucleic acid encoding the positive selection marker is located between the homology arms.

Where the vector is to be used for producing a recombinant microorganism in accordance with the invention it will be adapted in use to allow for the expression of the nucleic acids encoding the one or more selection marker. Accordingly, it will also include at least one promoter able to drive expression of the selection markers contained in the plasmid. The at least one promoter may comprise a part of the at least one nucleic acid sequence encoding at least one counter-selection marker or a part of the at least one nucleic acid sequence encoding at least one positive selection marker, or it may be a separate nucleic acid contained within the plasmid, which is separated from the nucleic acid(s) encoding the one or more selection markers by intervening nucleotides. In one embodiment, the promoter may be inducible. In another embodiment the promoter is constitutive.

Skilled persons will readily appreciate promoters of use in a plasmid of the invention. However, by way of example, these may include the Ppta-ack promoter (described herein in the Examples section), the lac promoter, ara, tet, or T7 system.

In one particular embodiment, the plasmid includes a strong promoter which is able to drive expression of the selection marker(s). In one embodiment, the plasmid includes a strong promoter to drive expression of at least a nucleic acid encoding a counter-selection marker. This is particularly the case where an altered PheS is used for counter-selection and the host genome includes a nucleic acid encoding PheS. Ideally the strong promoter will be sufficient to drive expression of the altered PheS at at least the same level, and preferably at an increased level, compared to expression of a nucleic acid encoding PheS which is present in the host genome. Alternatively, one or more other regulatory element, such as an operator and/or enhancer, could be included on the plasmid in addition to a promoter, to increase expression of one or more selection marker. Examples of strong promoters of use in the invention include, for example, T3 promoter, T7 promoter, PrRNA promoter, Ptrc promoter, or those exemplified in the Examples section hereinafter.

The at least one positive selection marker may be chosen from any number of known positive selection markers which will be readily appreciated by persons skilled in the area of technology to which the invention relates. However, by way of example, CatP (chloramphenicol acetyltransferase), ErmB or TetA could be used [Heap et al., 2009 (J Microbial Methods; July; 78(1); 78-85). Skilled persons will readily appreciate the nucleotide sequence for nucleic acids encoding these positive selection markers, based on published information, and the genetic code. However, by way of example, GenBank: WP_002570989 (CatP), YP_007078965 (ErmB), NP_957551.1 (TetA); CatP (SEQ ID 23); ErmB (SEQ ID 24); TetA (SEQ ID 25).

The homology arms allow for homologus recombination of the vector with the host genome. While it may be preferred that the arms have 100% complementarity to the region in the genome which they are targeted to, this is not necessary, provided that the sequence is sufficiently complementary to allow for targeted recombination with the genetic region of interest. Typically, the arms will have a level of homology which would allow for hybridisation to a target region under stringent conditions, as defined in Sambrook et al (Molecular Cloning: A laboratory manual, Cold Spring Harbor Laboratory Press, Cold Spring Harbor, N.Y., 1989). As will be appreciated by persons of skill in the art, the homology arms may be designed to hydridise to nucleic acid sequences within the genome which are adjacent to each other or separated from each other by one or more nucleotides.

Skilled persons will be able to readily design homology arms sufficient to allow for targeted homologous recombination having regard to publicly available sequence information for a given parental microorganism. Exemplary information is provided in the Examples section herein after.

A plasmid may also comprise one or more additional elements including one or more regulatory elements, one or more origin of replication, one or more multicloning site, among other elements. In one particular embodiment, the plasmids are adapted to allow for the disruption of a gene native to (or at least already present in) a parental microorganism, for example. In another embodiment, the plasmids are adapted to allow for integration and expression of one or more genes encoded by the plasmid. The plasmids may be in the form of naked nucleic acids as well as nucleic acids formulated with one or more agents to facilitate delivery to a cell (for example, liposome-conjugated nucleic acid, an organism in which the nucleic acid is contained).

As described herein before, phenylalanine tRNA synthetase is made up of two subunits, of which one is PheS. The second subunit may be present in the genome of a parental microorganism to be transformed. Accordingly, in the presence of a vector of the invention, a microorganism is able to produce phenylalanine tRNA synthetase, albeit one which is altered and able to aminoacylate tRNA using phenylalanine analogues. In addition, while the altered PheS may be based on PheS from any organism, as described previously herein, in a preferred embodiment it should be one which is compatible with the other subunit expressed by the parental microorganism. If the subunits are not compatible they will not form a functional enzyme. Skilled persons will readily be able to identify whether or not phenylalanine tRNA synthetase subunits are compatible using standard assays for testing the activity and function of the enzyme—as are described herein before. However, the inventors contemplate that a PheS from any *Clostridium* spp. will be compatible with a PheT subunit from any other *Clostridium* spp. In one particular embodiment, the PheS subunit is from the same species of Clostridia as the parental microorganism. In one particular embodiment, the altered PheS is based on the PheS of the phenylalanine tRNA synthetase expressed by the parental microorganism to be transformed. In another embodiment, the plasmid of the invention may also include a nucleic acid encoding a PheT subunit, which together with the altered PheS, forms an active phenylalanine tRNA synthetase, albeit an altered one able to aminoacylate tRNA using phenylalanine analogues. This may be useful, for example, where the parental microorganism does not contain a nucleic acid encoding the PheT subunit.

A plasmid may be replicating or non-replicating.

Nucleic acid vectors of use in the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual nucleic acids, including a nucleic acid encoding a counter-selection marker, nucleic acid encoding a positive selection marker, homology arms, nucleic acid of interest, and optionally other nucleic acids will be operably linked to one another so that they can perform their desired function.

Any one of a number of plasmid vectors known in the art may be suitable for use in the invention. However, by way of example, vectors from PMTL80000 series would be suitable. Specific examples are provided in the Examples section herein after.

In certain embodiments of the invention, a nucleic acid vector is one suitable for generating or cloning a nucleic acid encoding a ThiK or an altered PheS of the invention. In this case, the vector need not be adapted to express the ThiK or an altered PheS. Any number of known nucleic acid vectors may be used, including plasmids and viral vectors. Such vectors may include one or more regulatory elements, an origin of replication, a multicloning site and/or a selectable marker, among other elements, sites and markers, as will be known to persons skilled in the art.

Cells

The invention also provides a cell comprising a nucleic acid of the invention, a vector, a PheS and/or ThiK according to the invention. The cell may be of any origin and may include those of use in cloning or preparing a vector in accordance with the invention. In one embodiment, the cell is *E. coli* or a *Clostridium* spp.

Methods

As described herein before, the invention provides a method for the production of a recombinant microorganism from a parental microorganism. The method generally comprises at least the steps of: transforming a parental microorganism with a plasmid as described herein before, selecting one or more microorganisms that express at least the one positive selection marker and selecting one or more microorganisms which do not express the at least one counter-selection marker.

A parental microorganism may be transformed with a plasmid of the invention using any number of techniques known in the art for producing recombinant microorganisms. By way of example only, transformation (including transduction or transfection) may be achieved by electroporation, electrofusion, ultrasonication, polyethylene glycol-mediated transformation, chemical or natural competence, protoplast transformation, prophage induction or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

By way of example only, electroporation has been described for several carboxydotrophic acetogens such as C. ljungdahlii (Köpke et al. 2010, Poc. Nat. Acad. Sci. U.S.A. 107: 13087-92; Leang et al., 2012, Appl. Environ. Microbiol.; PCT/NZ2011/000203; WO2012/053905), and C. autoethanogenum (PCT/NZ2011/000203; WO2012/053905) and is a standard method used in many Clostridia such as C. acetobutylicum (Mermelstein et al., 1992, Biotechnology, 10, 190-195), C. cellulolyticum (Jennert et al., 2000, Microbiology, 146: 3071-3080) or C. thermocellum (Tyurin et al., 2004, Appl. Environ. Microbiol. 70: 883-890).

By way of further example, electrofusion has been described for acetogenic Clostridium sp. MT351 (Tyurin and Kiriukhin, 2012, J Biotech: 1-12).

A further exemplary technique includes the prophage induction described for carboxydotrophic acetogen such as C. scatologenes (Prasanna Tamarapu Parthasarathy, 2010, Development of a Genetic Modification System in Clostridium scatologenes ATCC 25775 for Generation of Mutants, Masters Project Western Kentucky University).

By way of further example, the conjugation methods of Herbert et al., 2003, (FEMS Microbiol. Lett. 229: 103-110) and Williams et al., 1990 (J. Gen. Microbiol. 136: 819-826) may be used.

It should be appreciated that the plasmid may be delivered to a parental microorganism as naked nucleic acid or may be formulated with one or more agents to facilitate the tranformation process (for example, liposome-conjugated nucleic acid, an organism in which the nucleic acid is contained).

In certain embodiments, due to the restriction systems which are active in the microorganism to be transformed, it is necessary to methylate any nucleic acid (for example a plasmid of the invention) to be introduced into the microorganism. This can be done using a variety of techniques, including those described below.

By way of example, in one embodiment, a recombinant microorganism of the invention is produced by a method comprises the following steps:

introduction into a shuttle microorganism of (i) at least one plasmid to be introduced to the parental microorganism as described herein and (ii) a methylation construct/vector comprising a methyltransferase gene;
expression of the methyltransferase gene;
isolation of the at least one plasmid from the shuttle microorganism; and,
introduction of the at least one plasmid into a destination microorganism.

In one embodiment, the methyltransferase gene is expressed consitutively. In another embodiment, expression of the methyltransferase gene is induced.

The shuttle microorganism is a microorganism, preferably a restriction negative microorganism, that facilitates the methylation of the nucleic acid sequences that make up a plasmid of the invention. In a particular embodiment, the shuttle microorganism is a restriction negative E. coli, Bacillus subtillis, or Lactococcus lactis.

The methylation construct/vector comprises a nucleic acid sequence encoding a methyltransferase.

Once the one or more plasmid and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism.

Expression of the methyltransferase enzyme results in methylation of the genes present on the one or more plasmid to be introduced to a parental microorganism. The plasmid may then be isolated from the shuttle microorganism according to any one of a number of known methods. For example, commercially available kits such as Qiagen or Zymo may be used according to the manufacturer's instructions.

In one particular embodiment, both the methylation construct/vector and the one or more plasmid of the invention are concurrently isolated.

The one or more plasmid destined for the parental microorganism may be introduced into the microorganism using any number of known methods. However, by way of example, the methodology described hereinbefore, or in the Examples section hereinafter may be used.

It is envisaged that a methyltransferase gene may be introduced into a shuttle microorganism and over-expressed. Thus, in one embodiment, the resulting methyltransferase enzyme may be collected using known methods and used in vitro to methylate one or more plasmid to be introduced into the parental microorganism. The one or more plasmid may then be introduced into the destination (parental) microorganism. In another embodiment, the methyltransferase gene is introduced into the genome of the shuttle microorganism followed by introduction of the one or more plasmid destined for the parental microorganism into the shuttle microorganism, isolation of the one or more plasid from the shuttle microorganism and then introduction of the one or more plasmid into the destination (parental) microorganism.

It is envisaged that the one or more plasmid destined for the parental microorganism and the methylation construct/vector as defined above may be combined to provide a composition of matter. Such a composition has particular utility in circumventing restriction barrier mechanisms to produce the recombinant microorganisms of the invention.

In one particular embodiment, the methylation construct/vector is a plasmid.

Skilled persons will appreciate a number of suitable methyltransferases of use in producing microorganisms in accordance with the invention. However, by way of example the Bacillus subtilis phage ΦT1 methyltransferase and the methyltransferase described in WO2012053905 may be used. Nucleic acids encoding suitable methyltransferases will be readily appreciated having regard to the sequence of the desired methyltransferase and the genetic code.

Any number of constructs/vectors adapted to allow expression of a methyltransferase gene may be used to generate the methylation construct/vector. However, by way of example those mentioned in WO2012053905 may be used.

Once a plasmid has been introduced into a desired parental microorganism, a first selection occurs. This involves selecting one or more microorganisms that express at least the one positive selection marker.

Such microorganisms may be identified and selected using any number of known techniques, having regard to the positive selection marker being used. However, by way of general example, the microorganisms may be cultured in or on a media which contains a toxin which would kill any microorganisms which do not express the positive selection marker. By way of specific example, the microorganisms may be grown in the presence of a toxic antibiotic, with the plasmid of the invention including a nucleic acid encoding a product conferring antibiotic resistance to the microorganism. Those microorganisms in which the plasmid is present will survive and those that do not will die.

Further examples of methodology and conditions of use in selecting microriganisms expressing a positive selection marker are described, for example, in Sambrook et al, 1989 (as previously described herein). Additional examples are provided in the Examples section herein after.

The methods of the invention also include a second selection. This involves selecting one or more microorganism that does not express at least one counter selection marker.

In the case of use of ThiK as a counter-selection marker, selection of one or more microorganisms which do not express this counter-selection marker involves culturing the microorganisms in or on a media containing a guanosine analgoue. In one particular embodiment, the guanosine analogue is ganciclovir. Those microorganisms which contain and express a nucleic acid encoding the ThiK counter-selection marker will not survive in the presence of the guanosine analogue. Accordingly, those microorganisms which survive are selected as having undergone the desired double-crossover recombination event.

In the case of use of an altered PheS as a counter-selection marker, selection of one or more microorganisms which do not express this counter-selection marker involves culturing the microorganisms in or on a media containing a phenylalanine analogue. In one particular embodiment, the phenylalanine analogue is as herein before exemplified. Those microorganisms which contain and express a nucleic acid encoding the altered PheS counter-selection marker will not survive in the presence of the phenylalanine analogue. Accordingly, those microorganisms which survive are selected as having undergone the desired double-crossover recombination event.

When using an altered PheS as a counter selection marker, it may be necessary to also include phenylalanine in the media.

The methods of the invention include both simultaneous and consecutive selection steps. For example, one could select microorganisms for single crossover events using the positive selection maker and subsequently select microorganisms for double crossover events using the counter-selection marker. Alternatively, the positive and counter-selection can occur simultaneously. By way of example, where the nucleic acid encoding the positive selection marker is positioned on the plasmid vector outside of the homology arms one may consecutively select for single-crossover events, then counter-select, selecting for the double-crossover events. By way of further example, where the nucleic acid encoding the positive selection marker is located between the homology arms (and is therefor integrated into the gemone of the parental microorganism), positive selection and counter-selection may occur simultaneously; any cell which has the positive selection marker integrated into the genome and is resistant to the counter-selection marker, will have had a double crossover event occur.

Any media suitable for the culturing of one or more microorganisms may be used in a method of the invention. Skilled persons will readily appreciate appropriate media based on published information and having regard to the nature of the invention and the parental microorganisms described herein. Preferably, the media will be a media in which little to no phenylalanine is present, or at least a level of phenylalanine which does not out-compete the phenylalanine analgoues during counter-selection. By way of example, any appropriate minimal medium would be suitable, such as: Clostiridia Minimal Medium, Minimal defined medium (MDM), supplemented defined medium (SDM) and complete defined medium (CDM). Specific examples are provided herein after in the Examples section.

Once one or more microorganism is selected in accordance with the invention, it may be cultured and optionally stored for future use using known methodology.

The invention will now be described, by way of example only, with reference to the following Examples.

EXAMPLES

The following examples describe construction of plasmids for counterselectable markers HSV-Tk and PheS*, functionality HSV-Tk and PheS* for of counterselection in *Clostridium autoethanogenum*, and use of HSV-Tk and PheS* to facilitate homologous recombination gene replacement on the genome of *Clostridium autoethanogenum*. The same principle can also be applied to other members of the *Clostridium* family, as the no homologue of the HSV-Tk gene exists in any sequenced *Clostridium* and the pheS genes or Clostridia species are highly conserved.

Standard Recombinant DNA and molecular cloning techniques were used in this invention and are described by Sambrook et al, 1989 and Ausubel et al, 1987. *E. coli* strain TOP10 (Life Technologies) and *Clostridium autoethanogenum* DSM10061 and DSM23693 (a derivate of DSM10061) were used. *E. coli* were grown in LB and SOB medium as described by Sambrook et al, 1989 and Ausubel et al, 1987, while *Clostridium autoethanogenum* was grown in anaerobic PETC medium (Table 1).

TABLE 1

PETC media (ATCC media 1754; atcc.org/Attachments/2940.pdf)

| Media component | Concentration per 1.0 L of media |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Yeast Extract | 1 g |
| Resazurin (2 g/L stock) | 0.5 ml |
| MES | 2 g |
| Reducing agent | 0.006-0.008% (v/v) |

TABLE 1-continued

| PETC media (ATCC media 1754; atcc.org/Attachments/2940.pdf) | |
|---|---|
| Distilled water | Up to 1 L, pH 5.5 (adjusted with HCl) |
| Wolfe's vitamin solution | per L of Stock |
| Biotin | 2 mg |
| Folic acid | 2 mg |
| Pyridoxine hydrochloride | 10 mg |
| Thiamine•HCl | 5 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Thioctic acid | 5 mg |
| Distilled water | To 1 L |
| Trace metal solution | per L of stock |
| Nitrilotriacetic Acid | 2 g |
| $MnSO_4$•$H_2O$ | 1 g |
| Fe $(SO_4)_2(NH_4)_2$•$6H_2O$ | 0.8 g |
| $CoCl_2$•$6H_2O$ | 0.2 g |
| $ZnSO_4$•$7H_2O$ | 0.2 mg |
| $CuCl_2$•$2H_2O$ | 0.02 g |
| $NaMoO_4$•$2H_2O$ | 0.02 g |
| $Na_2SeO_3$ | 0.02 g |
| $NiCl_2$•$6H_2O$ | 0.02 g |
| $Na_2WO_4$•$2H_2O$ | 0.02 g |
| Distilled water | To 1 L |
| Reducing agent stock | per 100 mL of stock |
| NaOH | 0.9 g |
| Cystein•HCl | 4 g |
| Na2S | 4 g |
| Distilled water | To 100 mL |

Example 1

Functionality of HSV-Tk and PheS* for of Counterselection in Clostridium autoethanogenum Construction of Plasmids:

Construction of plasmids containing Hsv-tk: DNA sequence of Human Herpes Virus thymidine kinase (Hsv-tk) was obtained from NCBI (Nucleic acid and amino acid). The codons in Hsv-tk gene were optimized to suit C. autoethanogenum and synthesized by GeneArt and delivered in their standard vector pMK-RQ (Seq. ID. 1—pMK-RQ-HSV-tk)).

HSV-tk was released from pMK-RQ vector by digesting with NdeI and NheI restriction enzymes (New England Biolabs) and cloned into a modified version of the E. coli-Clostridium shuttle vector pMTL83151 (FJ797651.1; Nigel Minton, University of Nottingham; Heap et al., 2009) which is referred to as pMTL83155 (SEQ ID 3), between the same sites in E. coli strain TOP10 (Life Technologies) to create pMTL83155-Hsv-tk (Seq. ID. 2, FIG. 1). The pMTL83155 plasmid contains the promoter sequence of C. autoethanogenum phosphate acetyl transferase gene between NotI and NdeI sites (Seq. ID. 3).

Construction of mutated pheS*: The native pheS was identified in the genome from the sequence of C. autoethanogenum DSM 10061 (Seq.ID.12). By comparing the sequence of E. coli MG1655 (Seq. ID. 13) and C. autoethanogenum's pheS by sequence alignment, the putative substrate specificity site was identified based upon homology of the amino acid sequence of amino acids between G284 and G298 of E. coli (amino acid sequence of PheS from E. coli MG1655 is SEQ ID 20) and amino acids G301 and G315 of C. autoethanogenum (FIG. 3). A single point mutation was introduced at base 932, substituting C for G, resulting in the codon encoding glycine instead of alanine (Seq. ID. 14).

Figure 4:
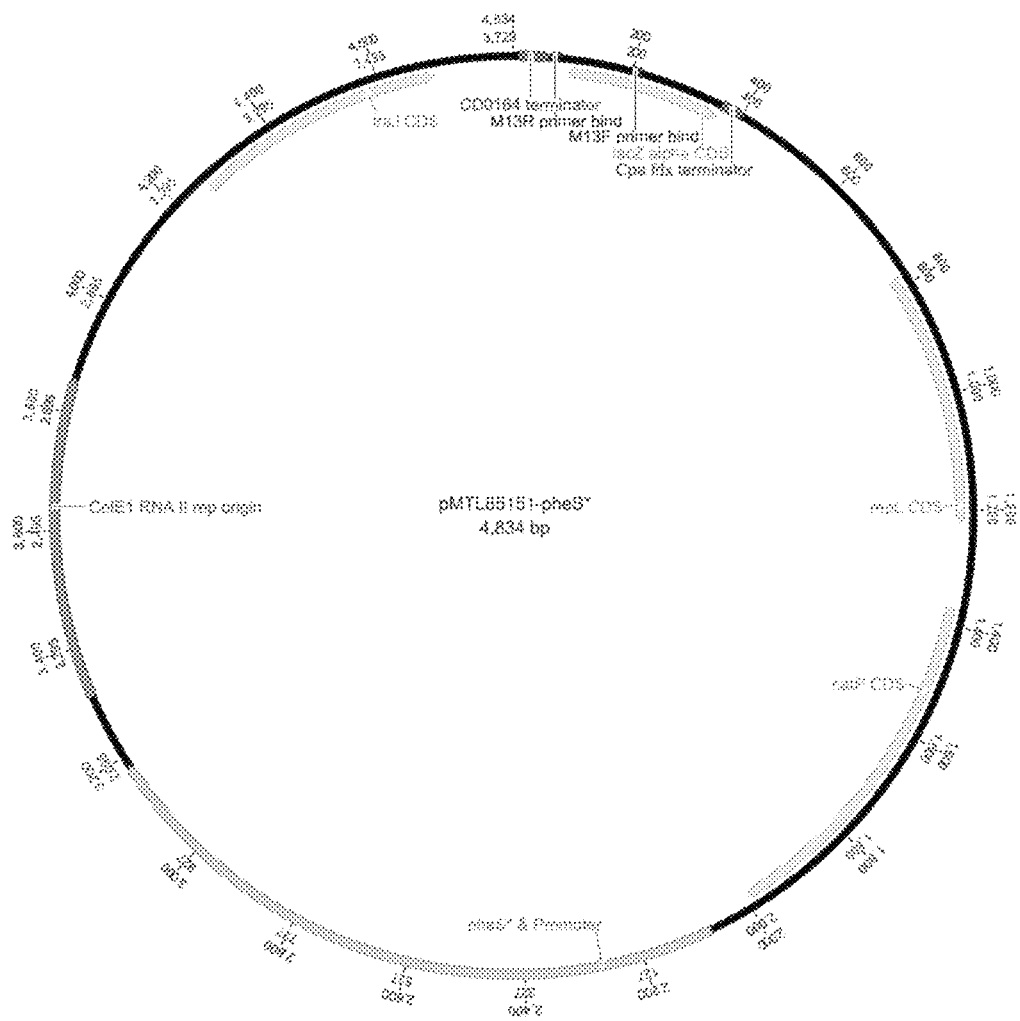
FIG. 4: Shows the map of plasmid pMTL85151-pheS*
Figure 5:
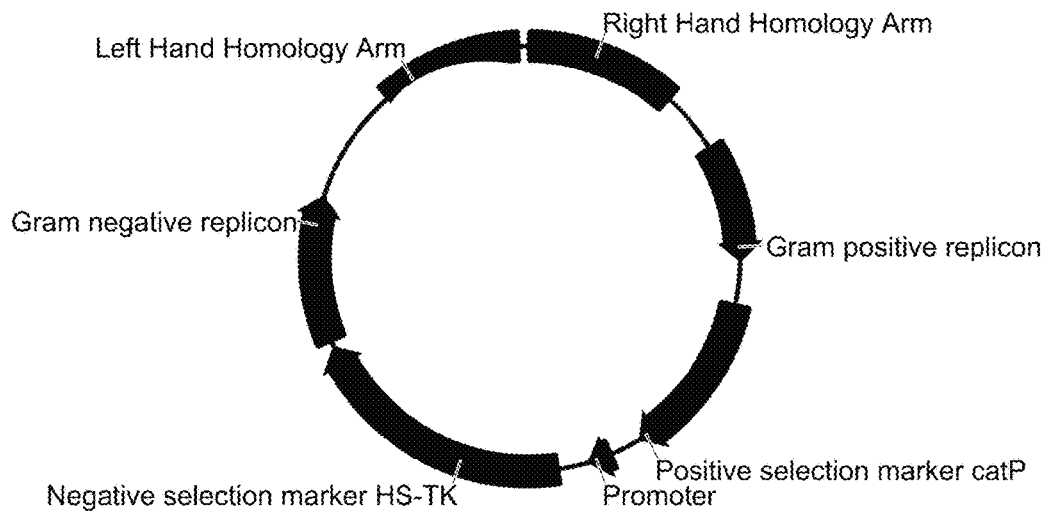
FIG. 5: Shows a representative map of a plamid comprising HSV-tk.
Figure 6:
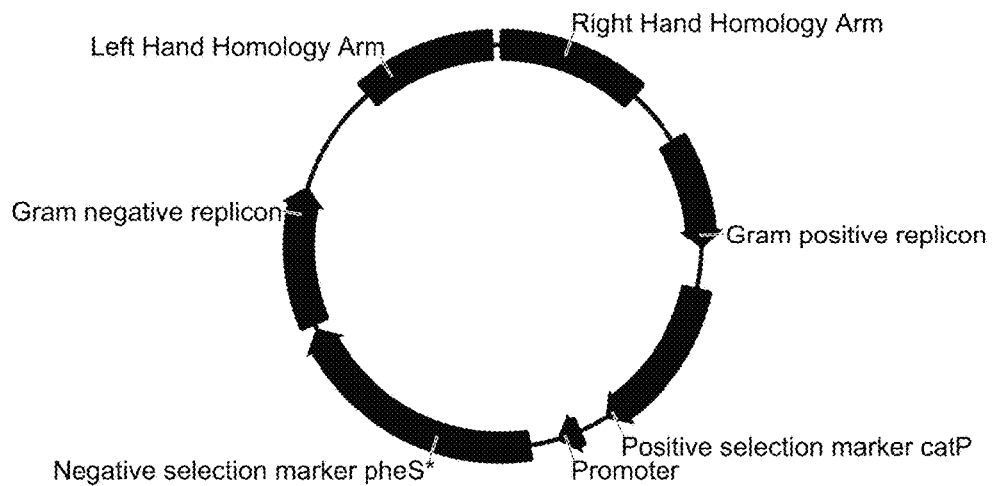
FIG. 6: Shows a representative map of a plamid comprising pheS.

Construction of plasmids containing pheS*: The modified pheS* was transcriptionally coupled to a synthetic promoter and RBS site (PpheS*; Seq.ID. 17) upstream of the start codon to allow high constitutive expression. The construct was also flanked by PmeI restriction sites to enable cloning of the gene into alternative vectors. Synthesis and subcloning into vector pMTL85151 utilizing restriction enzyme PmeI was carried out by GeneArt resulting in the final vector pMTL85151-pheS* (Seq. ID. 18; FIG. 4).

Sensitivity Testing:

Toxicity testing of DL-4-chlorophenylanine: E. coli Top10 and C. autoethanogenum DSM23693 harbouring the empty vector pMTL85151 were grown initially in the presence of DL-4-chlorophenylanine on plates and in liquid media to ascertain if the counter-selection marker has any effect on growth of the organisms. It was noted that the chemical did not impede growth of either organism in liquid media or on plates and colonies grew to the same size after 24/48 hours for E. coli and C. autoethanogenum, respectively.

Testing pheS* in E. coli: To test the ability of the counter selection marker to work in E. coli, the plasmid pMTL85151-pheS* was transformed into TOP10 and grown under chloramphenicol selection only. Once the culture had reached an OD of 0.5, representing an exponential growth phase, 100 ul was plated onto LB plates containing chloramphenicol and DL-4-chlorophenylalanine as well as chloramphenicol alone as a control, in triplicate, and incubated for 24 hours at 37° C. After 24 hours the plates were inspected and noted that on the chloramphenicol plates alone, there was a lawn of large colonies as expected, however, on the plates containing both chloramphenicol and DL-4-chlorophenylalanine, there was a light shading of small colonies suggesting that DL-4-chlorophenylanine was affecting the growth of the E. coli harbouring pMTL85151-pheS*. After 36 hours, the double selection plates had outgrown to the same level as the chloramphenicol alone plates.

Transformation of C. Autoethanogenum and Confirmation of Plasmids:

Transformation of C. autoethanogenum: The pMTL83155, pMTL83155-Hsv-tk and pMTL85155-PheS plasmids were introduced into C. autoethanogenum DSM23693 (a derivate of DSM10061) as described in WO2012053905. Outgrowth was performed in PETC broth and spread on PETC-agar media supplemented with 15 μg/ml thiamphenicol (Sigma) and 10 μg/ml trimethoprim (Sigma). Colonies were observed after 3 days of incubation at 37° C. in pressurized gas jars with 20 psi of a gas mix of 48% $CO_3$ 2% H2, 20% $CO_2$, 30% N2. Streaks of single colonies were made on PETC-agar media containing 15 μg/ml thiamphenicol.

Screening of transformants for the presence of plasmids: 2 colonies from LZ-pMTL83155 and LZ-pMTL83155-hsv-tk transconjugantswere randomly screened for the presence of pMTL83155 and pMTL83155-Hsv-tk plasmidsby PCR using primers repHf (Seq. ID. 4) and catr (Seq. ID. 5) spanning the Gram-positive replicon and catP positive selection marker in pMTL83155 and pMTL83155-Hsv-tk. Unmodified C. autoethanogenum was used as a control in these PCRs. The Maxime PCR PreMix Kit was used for PCR. 16s rDNA was also PCR amplified from these transformants using primers fD1 (Seq. ID. 6) and rP2 (Seq. ID.7) and Maxime PCR PreMix Kit.

Figure 2:
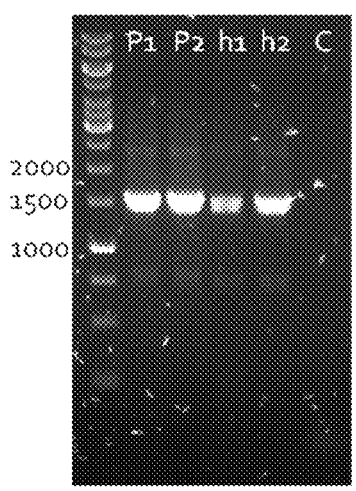
FIG. 2: Shows PCR amplification of ~1.5 kb fragment spanning gram positive replicon and catP marker on pMTL83155 and pMTL83155-Hsv-tk (h1 and h2) in *C. autoethanogenum* transformants. Unmodified *C. autoethanogenum* (C) was used as a control. 2 colonies each of LZ-pMTL83155 (P1 and P2) and LZ-pMTL83155-Hsv-tk (h1 and h2) were screened.

PCR with repHF and catR primers amplified ~1.5 kb bands from LZ-pMTL83155-1 and -2 and LZ-pMTL83155- hsv-tk-1 and -2 (FIG. 2). No amplification was detected from unmodified *C. autoethanogenum* sample, confirming the presence of plasmids only in the transformants. The sequencing of 16s rRNA from LZ-pMTL83155-1 (Seq. ID. 8) and -2 (Seq. ID. 9) and LZ-pMTL83155-hsv-tk-1 (Seq. ID. 10) and -2 (Seq. ID. 11) further confirmed the clones to be *C. autoethanogenum*.

Confirmation of *C. autoethanogenum* transformants harbouring plasmid pMTL85151-pheS* was carried out on three independent colonies using PCR primers specific to the plasmid (Seq. ID. 15 and 16), and primers fD1 (Seq. ID. 6) and rP2 (Seq. ID.7) to sequence the 16s rRNA.

Functionality of HSV-Tk and PheS* as Counterselectable Markers in *Clostridium autoethanogenum*:

Sensitivity of *C. autoethanogenum* transformants to ganciclovir: The sensitivity of LZ-pMTL83155 and LZ-pMTL83155-hsv-tk to ganciclovir was tested by plating them on PETC agar media containing 20 nM ganciclovir only and PETC agar media containing 20 nM ganciclovir and 15 µg/ml thiamphenicol. Colonies on ganciclovir plates were observed only with LZ-pMTL83155 transformants and not with LZ-pMTL83155-hvs-tk (Table 2). The presence of Hvs-tk gene confers toxicity to ganciclovir.

Sensitivity of *C. autoethanogenum* harbouring plasmid pMTL85151-pheS* to DL-4-chlorophenylanine: The three independent transformants of *C. atoethanogenum* DSM23693 harbouring pMTL85151-pheS*, as well as *C. autoethanogenum* DSM23693 harbouring pMTL85151, were grown in liquid PECT media supplemented with thiamphenicol and grown at 37° C. under CO only conditions. After 24 hours, 100 ul of each of the three independent, as well as the control pMTL85151, were plated into PETC-MES agar supplemented with either thiamphenicol alone, or thiamphenicol and DL-4-chlorophenylalanine and incubated for 48 hours. After 48 hours, the plates were inspected and the plates containing only thiamphenicol had a lawn of colonies for all 4 strains, whereas, the plates containing double selection only had 3, 4, and 7, colonies for each of the independent transformants containing pheS*, in contrast, the *C. autoethanogenum* transformants harbouring pMTL85151 showed the same results as the thiamphenicol only plate, suggesting DL-4-chlorophenylalanine has no effect upon this strain.

TABLE 2

Sensitivity of *C. autoethanogenum* transconjugants to different prodrugs in the presence of corresponding CSM

| CSM | Prodrug | Concentration | LZ-pMTL83155 | LZ-pMTL83155-hsv-tk |
|---|---|---|---|---|
| Hsv-tk | Ganciclovir | 20 nM | Lawn | 0-5 |
| PheS | DL-4-Chlorophenlanine | 0.20% | Lawn | 7-Mar |

This demonstrateds that both HSV-Tk and PheS* in combination with prodrugs Ganciclovir and DL-4-Chlorophenlanine are effective for counterselection in *C. autoethanogenum*

Example 2

Use of PheS* to Facilitate Homologous Recombination Gene Replacement on the Genome of *Clostridium autoethanogenum*

This example describes replacing a native *Clostridium autoethanogenum* R-specific 2,3-butanediol dehydrogenase gene with S-specific 2,3-butanediol dehydrogenase gene from *Klebsiella pneumoniae* through homologous recombination facilitated by PheS* as a counter selectable marker in *Clostridium autoethanogenum* DSM23693 that has an inactivated secondary alcohol dehydrogenase.

Figure 8:
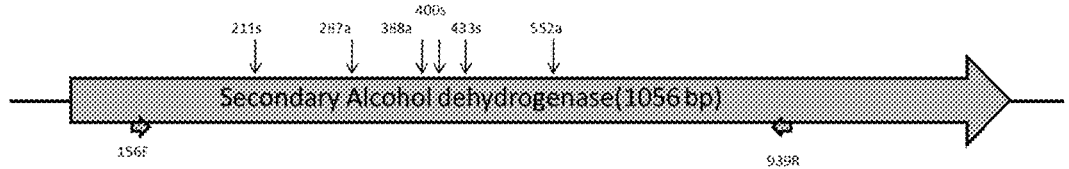
FIG. 8: Gene map showing the intron target sites (211s, 287a, 388a, 400s, 433s, and 552a). Primer binding sites are also shown (bottom, horizontal arrows).

Construction of *C. autoethanogenum* DSM23693 Strain that has an Inactivated Secondary Alcohol Dehydrogenase A strain of *Clostridium autoethanogenum* DSM23693 was constructed that has an inactivated secondary alcohol dehydrogenase (Nucleic acid sequence of primary:secondary alcohol dehydrogenase of *C. autoethanogenum*) using the ClosTron System. (Heap et al 2007). The intron design tool hosted on the ClosTron.com website was used to design a 344 bp targeting region (Intron targeting region), as well as identify six target sites (FIG. 8) on the sense and antisense strands. The targeting region was chemically synthesised in the vector pMTL007C-E2 containing a Retro-transposition Activated ermB marker (RAM).

Figure 9A:
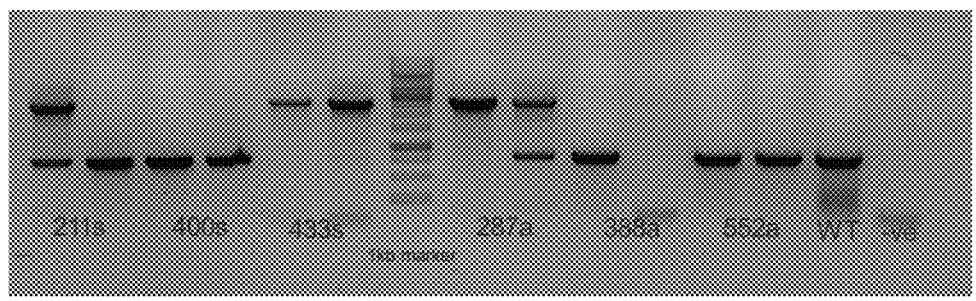
FIG. 9A-9C: Confirmation of the group II intron insertions.
Figure 9B:
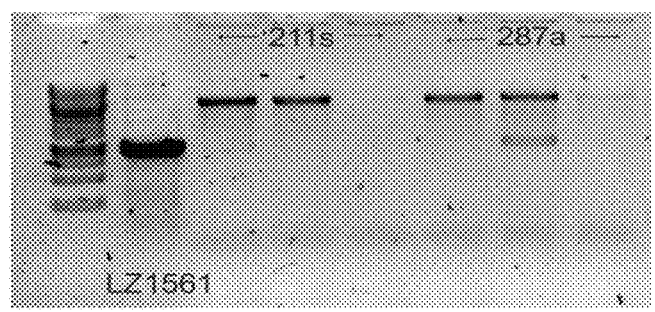
Figure 9C:
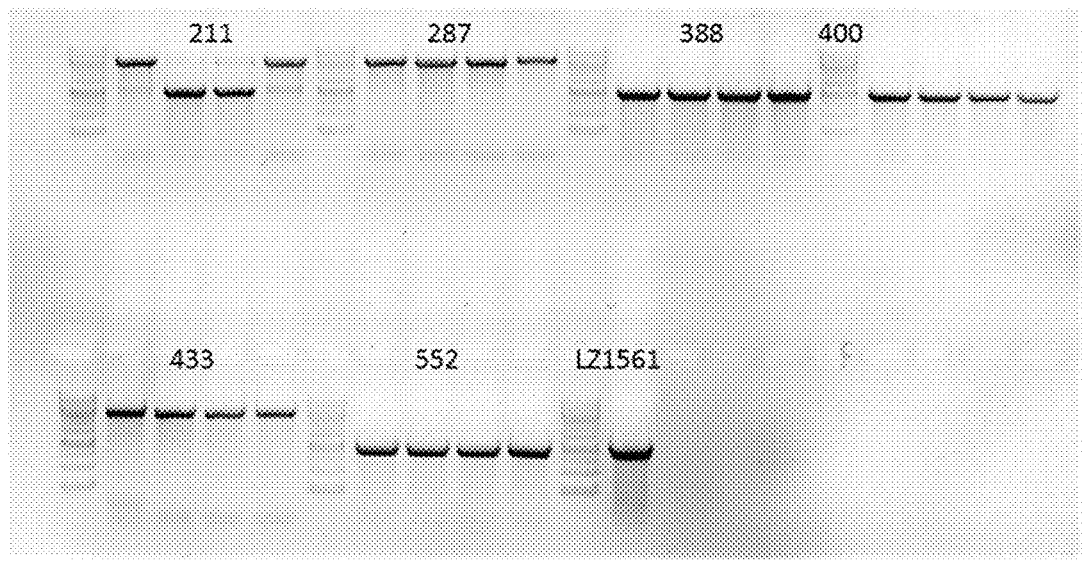

The vectors were introduced into *C. autoethanogenum* DSM23693 as described in WO2012/053905. Single colonies grown on PETC MES with 15 µg/ml thiamphenicol were streaked on PETC MES with 5 µg/ml clarothromycin. Colonies from each target were randomly picked, and screened for the insertion using flanking primers 155F, and 939R. Amplification was performed using the iNtron Maxime PCR premix. A PCR product of 783 bp indicated a wild-type genotype, while a product size of approximately 2.6 kb suggests the insertion of the group II intron in the target site (FIG. 9). The loss plasmid was checked by amplification of the resistance marker (catP), and the gram positive origin of replication (pCB102). This strain was used as base strain replacing a native *Clostridium autoethanogenum* R-specific 2,3-butanediol dehydrogenase gene with S-specific 2,3-butanediol dehydrogenase gene from *Klebsiella pneumoniae* through homologous recombination facilitated by PheS*.

Construction of plasmid pPheS-ErmB. The fragment containing PheS* cassette (Nucleic acid sequence of pPheS Fragment PCR product for assembly of pPheS-CaBD-HXXKpBDH) and ColE1 with traJ (Nucleic acid sequence of PheS* cassette and ColE1 with traJ PCR product for assembly of pPheS*-ErmB) ) was amplified from pMTL85151-PheS* (Seq ID No. 18) with primers PheS-repH-F (SEQ ID No. 28) and traJ-ermB-R (SEQ ID No. 29). The fragment containing pCB102 origin of replication (Nucleic acid sequence of pCB102 origin of replication PCR product used for assembly of pPheS*-ErmB) was amplified from the pMTL80000 series (Heap et al., 2009) using primers RepH-ermB-F (SEQ ID No. 31) and RepH-pheS-R (SEQ ID No. 32). The erythromycin resistance cassette (Nucleic acid sequence of erythromycin resistance cassette PCR product used for assembly of pPheS*-ErmB) was amplified from the pMTL80000 series (Heap et al., 2009) using primers ermB-traJ-F (SEQ ID No. 34) and ermB-repH-R ((SEQ ID No. 35). The described PCR products contained overlaps to facilitate seamless assembly. They were assembled using the GENEART Seamless Cloning and Assembly kit from Life Technologies. The resulting plasmid, pPheS*-ErmB was verified by restriction digestion and fragment analysis.

PCR amplification of plasmid parts for homologous recombination. The vector backbone containing PheS* (Nucleic acid sequence of pPheS Fragment PCR product for assembly of pPheS-CaBDHXXKpBDH) was amplified from pPheS*-ErmB (Nucleic acid sequence of pPhes-ErmB template for amplification of backbone plasmid for assembly of pPheS-CaBDHXXKpBDH) using primers AM015 (SEQ ID No. 37) and AM035 (SEQ ID No. 38). The upstream homology arm (Nucleic acid sequence of upstream homology arm PCR product for assembly of pPheS-CaBDHXXK-pBDH) was amplified from *C. autoethanogenum* genomic DNA using primers AM016 (SEQ ID No. 40) and AM017 (SEQ ID No. 41). The *K. pneumoniae* butanediol dehydrogenase gene (Nucleic acid sequence of *K. pneumoniae* butanediol dehydrogenase gene PCR product for assembly of pPheS-CaBDHXXKpBDH) was amplified, using primers AM018 (SEQ ID No. 43) and AM019 (SEQ ID No. 44), from pMTL85141-P-alsS-budA-budC (Kopke et. al. 2014). The chloramphenicol acetyltransferase expression cassette (Nucleic acid sequence of chloramphenicol acetyltransferase cassette PCR product for assembly of pPheS-CaBDHXXKpBDH) was amplified from the pMTL80000 series (Heap et al., 2009) using primers AM020 (SEQ ID No. 46) and AM021 (SEQ ID No. 47). The downstream homology arm (Nucleic acid sequence of downstream homology arm PCR product for assembly of pPheS*-CaBDHXXKpBDH) was amplified from *C. autoethanogenum* genomic DNA using primers AM022 (SEQ ID No. 49) and AM036 (SEQ ID No. 50).

Construction of pheS* containing plasmid for homologous recombination. The PCR products above contained overlaps to facilitate seamless assembly. They were assembled using the GENEART Seamless Cloning and Assembly kit from Life Technologies. The resulting plasmid, pPheS*-CaBDHXXKpBDH was verified by restriction digestion and fragment analysis.

Figure 7:
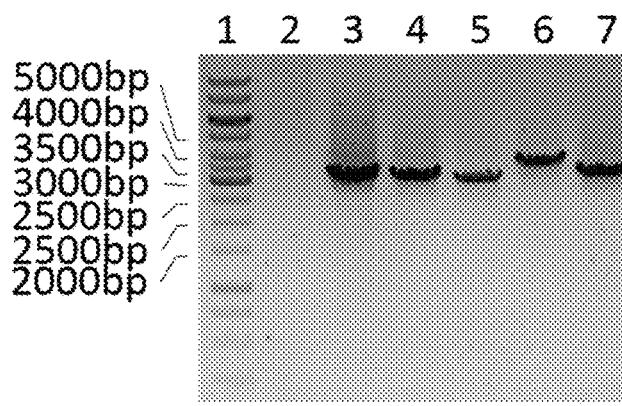
FIG. 7: Shows TAE agarose gel electrophoresis results from PCR screen with AM041 and AM042. Lane 1 contains GeneRuler 1 kb Ladder (Thermo). Lane 2 contains PCR with no template added. Lane 3 PCR with wild type *C. autoethanogenum* genomic DNA as template showing expected wild type product size (3137 bp). Lanes 4-7 contain PCR with p-chlorophenylalanine and thiamphenicol resistant colonies as template. Lane 6 shows a PCR product of expected size (3570 bp) for successful double crossover replacement of native butanediol dehydrogenase gene with butanediol dehydrogenase gene from *K. pneumonia*.

Introduction of plasmid, counter selection, and screening for integration. The pPheS*-CaBDHXXKpBDH was introduced as described in WO2012053905 into a strain of *C. autoethenogenum* DSM23693 that has a ClosTron-inactivated secondary alcohol dehydrogenase at position 287 as described above. Transformants were selected by their ability to grow on PETC-agar medium supplemented with 15 μg/ml thiamphenicol (Sigma) and 10 μg/ml trimethoprim (Sigma). To select for successful homologous recombination double cross, colonies were restreaked on PETC-agar medium supplemented with 15 μg/ml thiamphenicol and 2 mg/ml p-chlorophenylalanine. Colonies which grew were screened for integration by PCR with primers AM041 (SEQ ID No. 51) and AM042 (SEQ ID No. 52) which flank the integration site outside the homology arms. Successful integration was identified as yielding a PCR product 3570 base pairs in length compared to 3137 base pairs for the wild type (FIG. 7). The PCR product was sequenced for fidelity by Sanger sequencing and found to be exactly the expected insertion sequence, confirming successful integration of the fragment facilitated by the pheS* counterselectable marker.

TABLE 3

Primers used in Example 2

| Primer name | Sequence | SEQ ID |
|---|---|---|
| AM015 | CTTGCCTTGCTCGTCGGT | 37 |
| AM016 | GACGAGCAAGGCAAGCAATTATAGTGAAAGATGTGAAGG | 40 |
| AM017 | ACCTTTTTCATAATTATCTCTCCTTTTTTATAATAGTATGG | 41 |
| AM018 | AGAGATAATTATGAAAAAGGTTGCATTAGTTAC | 43 |
| AM019 | CCTTACAATTTAATTAAATACCATACCACCGTC | 44 |
| AM020 | GTATTTAATTAAATTGTAAGGATCCTAGTCAG | 46 |
| AM021 | GTACTTTTTATGAGCTCTTAACTATTTATCAATTC | 47 |
| AM022 | AGAGCTCATAAAAAGTACTCATAGAATTGATTAAAAAATG | 49 |
| AM035 | AAGTGATAGTCAAAAGGCATAACAGTG | 38 |
| AM036 | ATGCCTTTTGACTATCACTTATACATCTCCTTTAAATCCATTTG | 50 |
| AM041 | CTGGAAAAGAACTCTTAGC | 51 |
| AM042 | TGCGGTGGAATACAATGG | 52 |
| PheS-repH-F | GCAAGTTGAAAAATTCACGAAAGTTACACGTTACTAAAGG | 28 |
| traJ-ermB-R | CACTATCAACACACTCTTAAGCTTGCCTTGCTCGTCGGTG | 29 |
| RepH-ermB-F | GCTTTTGTAAATTTGCATAAAAATAAGAAGCCTGCATTTG | 31 |
| RepH-pheS-R | TTTAGTAACGTGTAACTTTCGTGAATTTTTCAACTTGCC | 32 |
| ermB-traJ-F | CACCGACGAGCAAGGCAAGCTTAAGAGTGTGTTGATAGTG | 34 |
| ermB-repH-R | GCTTCTTATTTTTATGCAAATTTACAAAAGCGACTCATAG | 35 |

The same strategy and plasmid can also be applied to *C. ljungdahlii* or *C. ragsdalei*. Transformation protocols have been described (WO2012/053905) (Leang, Ueki, Nevin, & Lovley, 2012).

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A modified phenylalanine tRNA synthetase (PheS) that aminoacylates tRNA with a phenylalanine analogue, wherein the modified PheS has the sequence of SEQ ID NO: 21, except with glycine instead of alanine at amino acid position 311.

2. The modified PheS of claim 1, wherein the phenylalanine analogue is selected from the group consisting of chlorophenylalanine, fluorophenylalanine and bromophenylalanine.

3. The modified PheS of claim 2, wherein the phenylalanine analogue is selected from the group consisting of DL-4-chlorophenylalanine, p-chlorophenylalanine, p-fluoro-L-phenylalanine, p-fluoro-DL-phenylalanine, and p-bromo-L-phenylalanine.

* * * * *